United States Patent [19]

Hirai et al.

[11] Patent Number: 5,028,738
[45] Date of Patent: Jul. 2, 1991

[54] PROCESS FOR PRODUCING 2-OXO-3-AROMATIC CARBOXYLIC ACID DERIVATIVES

[75] Inventors: Kenji Hirai, Sagamihara; Kazumi Nakamura, Abiko; Atsuko Fujita, Chiba, all of Japan

[73] Assignee: Sagami Chemical Research Center, Tokyo, Japan

[21] Appl. No.: 474,093

[22] PCT Filed: Sep. 11, 1989

[86] PCT No.: PCT/JP89/00928
 § 371 Date: May 2, 1990
 § 102(e) Date: May 2, 1990

[87] PCT Pub. No.: WO90/02725
 PCT Pub. Date: Mar. 22, 1990

[30] Foreign Application Priority Data

Sep. 13, 1988 [JP] Japan ............ 63-227414
Nov. 11, 1988 [JP] Japan ............ 63-283809
Nov. 11, 1988 [JP] Japan ............ 63-283810
Mar. 10, 1989 [JP] Japan ............ 1-56114
Mar. 10, 1989 [JP] Japan ............ 1-56115
Mar. 10, 1989 [JP] Japan ............ 1-56116

[51] Int. Cl.$^5$ ................................ 562 459
[52] U.S. Cl. .................. 562/459; C07C/59/74
[58] Field of Search ........................ 562/459

[56] References Cited

U.S. PATENT DOCUMENTS 4,334,089 6/1982 Kraas ................ 562/459
4,390,702 6/1983 Misaki ............... 562/459

Primary Examiner—Paul J. Killos
Attorney, Agent, or Firm—Wenderoth, Lind & Ponack

[57] ABSTRACT

There is a process for producing 2-oxo-3-aromatic carboxylic acid derivatives which comprises reacting aromatic pyruvic acid derivatives with electrophilic compounds in the presence of bases in a protic solvent. According to this process, 2-oxo-3-aromatic carboxylic acid derivatives which can be easily converted to aromatic amino acid derivatives or 2-aromatic carboxylic acid derivatives as important synthetic intermediates of medicines and agricultural chemicals can be produced in good yields with high selectivity.

13 Claims, No Drawings

PROCESS FOR PRODUCING 2-OXO-3-AROMATIC CARBOXYLIC ACID DERIVATIVES

TECHNOLOGICAL FIELD

This invention relates to a novel process for producing 2-oxo-3-aromatic carboxylic acid derivatives, and more specifically, this invention pertains to a process for producing 2-oxo-3-aromatic carboxylic acid derivatives of the following general formula (IV), (V) or (VI)

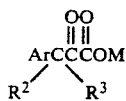  (IV)

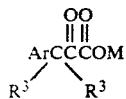  (V)

  (VI)

wherein Ar represents an aromatic group, $R^2$ represents a hydrogen atom or a substituted or unsubstituted alkyl, cycloalkyl, alkenyl, alkynyl or aralkyl group, $R^3$ represents a substituted or unsubstituted alkyl, cycloalkyl, alkenyl, alkynyl or aralkyl group, $R^4$ represents a substituted or unsubstituted alkylene group having 2 or more carbon atoms, and M represents a hydrogen atom, an alkali metal or alkaline earth metal atom.

BACKGROUND TECHNOLOGY

Double carbonylation reaction of benzyl halides using a cobalt carbonyl catalyst has previously been known as a method of producing 2-oxo-3-aromatic carboxylic acid derivatives. This reaction, however, gives a low yield and selectivity and requires limited starting materials. Accordingly, it cannot always give 2-oxo-3-aromatic carboxylic acid derivatives having the desired substituents [see, for example, M. Foa and F. Francalanci, J. Mol. Cat., 41, 89 (1987)].

It is known on the other hand that 2-oxo-3-aromatic butanoic acid esters are obtained by ring-opening isomerization reaction of β-aryl-β-methylglycidic acid esters with acid catalysts. This method cannot give other carboxylic acid derivatives. Moreover, depending upon an acid catalyst used, the yield and selectivity are both low (see, for example, Japanese Patent Publications Nos. 35068/1978 and 35069/1978 and Japanese Laid-Open Patent Publications Nos. 149970/1978 and 99445/1981).

Rearrangement reaction of α,β-dialkyl-β-aromatic glycidic acid esters with acids is known as a method of producing 2-oxo-3-aromatic carboxylic acid derivatives having two substituents at the 3-position [for example, see J. Am. Chem. Soc., 9-,8 4581 (1976) and J. Org. Chem., 40, 1741 (1975)]. However, this method is only known for the synthesis of compounds having limited substituents. Moreover, depending upon the acid catalyst used, the yield and selectivity are very low, and the method cannot be said to be a commercially efficient method.

A method of producing 3-(3',4'-dimethoxyphenyl)-3-methyl-2-butanone by oxidation with selenium and a method of producing 2-cyano-3,3-disubstituted carboxylic acid derivatives by autoxidation are also known [see Acta Pharm. Suec., 13, 65 (1976) and J. Org. Chem., 35, 3240 (1970)]. These methods, however are limited in respect of substituents, and the yields are low. Hence, they cannot be said to be general commercial manufacturing methods.

Thus, by the conventional processes, 2-oxo-3-aromatic carboxylic acid derivatives having the desired substituent at the 3-position cannot be produced conveniently with simplicity in good yields. It is an object of this invention to provide a commercially effective process for producing 2-oxo-3-aromatic carboxylic acid derivatives which are important synthetic intermediates for the production of medicines and agricultural chemicals.

DISCLOSURE OF THE INVENTION

The present inventors found, as a result of extensively studying a process for production of 2-oxo-3-aromatic carboxylic acid derivatives, that by reacting an aromatic pyruvic acid derivative with a suitable electrophilic reagent in the presence of a base in a protic solvent, the desired 2-oxo-3-aromatic carboxylic acid derivative can be synthesized in good yields and with good selectivity. This discovery has led to the present invention.

Thus, according to this invention, there is provided a process for producing 2-oxo-3-aromatic carboxylic acid derivatives represented by the following general formula

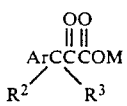  (IV)

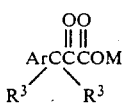  (V)

or

  (VI)

wherein Ar represents an aromatic group, $R^2$ represents a hydrogen atom or a substituted or unsubstituted alkyl, cycloalkyl, alkenyl, alkynyl or aralkyl group, $R^3$ represents a substituted or unsubstituted alkyl, cycloalkyl, alkenyl, alkynyl or aralkyl group, $R^4$ represents a substituted or unsubstituted alkylene group having 2 or more carbon atoms, and M represents a hydrogen atom, an alkali metal or alkaline earth metal atom, which comprises reacting an aromatic pyruvic acid derivative represented by the following formula

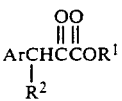  (I)

wherein Ar and $R^2$ are as defined above, and $R^1$ represents a hydrogen atom, a lower alkyl group, an alkali metal or alkaline earth metal atom,
with an electrophilic compound represented by the general formula $$R^3-X^1 \qquad (I)$$

or $$X^1-R^4-X^2 \qquad (III)$$

wherein $R^3$ and $R^4$ are as defined above, and $X^1$ and $X^2$ each represent a leaving group,
in the presence of a base in a protic solvent.

The process of this invention will be described in greater details below.

The term "lower" used in the present specification means that atomic groupings or compounds qualified by this term have not more than 6 carbon atoms, preferably not more than 4 carbon atoms.

The "aromatic group" means both carbocyclic groups and heterocyclic groups, and suitable examples of the aromatic group specifically include a phenyl group, a naphthyl group, an anthryl group, a furyl group, a thienyl group, a pyrrolyl group, an imidazolyl group, a pyrazolyl group, a pyridyl group, a pyrazinyl group, an indolyl group, a quinoxalyl group, a quinolyl group and an isoquinolyl group. These groups may be substituted by at least one, especially 1 to 3 substituents which do not adversely affect the reaction, for example, halogen atoms, alkyl groups, lower alkoxy groups, a phenoxy group, a hydroxyl group, lower alkoxycarbonyl groups, carboxy group and a methylene dioxy group. Especially preferable aromatic groups in this invention include phenyl, o-chlorophenyl, m-chlorophenyl, p-chlorophenyl, o-fluorophenyl, m-fluorophenyl, p-fluorophenyl, o,p-dichlorophenyl, m,p-dichlorophenyl, o,p-difluorophenyl, 2,4,6-trichlorophenyl, p-methylphenyl, o,p-dimethylphenyl, m,p-dimethylphenyl, p-ethylphenyl, p-propylphenyl, p-isobutylphenyl, p-octylphenyl, p-methoxyphenyl, p-ethoxyphenyl, p-butoxyphenyl, m,p-dimethoxyphenyl, p-phenoxyphenyl, m,p-methylenedioxyphenyl, m,p-(di-methyl-methylene)dioxyphenyl, p-methoxycarbonylphenyl, p-ethoxycarbonylphenyl, p-hydroxycarbonylphenyl, 1-naphthyl, 2-naphthyl, 6-methoxy-2-naphthyl, 2-anthranyl, 2-furyl, 3-furyl, 3-methyl-2-furyl, 4-methyl-2-furyl, 2-thienyl, 3-methyl-2-thienyl, 4-methyl-2-thienyl, 2-pyrrolyl, 1N-methyl-2-pyrrolyl, 4-imidazolyl, 1N-methyl-4-pyrazolyl, 2-pyridyl, 3-pyridyl, 4-pyridyl, 3-methyl-2-pyridyl, 4-methyl-2-pyridyl, 2-pyrazinyl, 3-indolyl, 1N-methyl-3-indolyl, 2-quinoxalyl, 2-quinolyl and 2-isoquinolyl groups.

The "alkyl group" may be linear or branched, and preferably contains up to 12 carbon atoms. Specific examples include methyl, ethyl, propyl, isopropyl, butyl, t-butyl, cyclopropylmethyl, pentyl, 2-pentyl hexyl, octyl, and dodecyl groups. These alkyl groups may be substituted by at least one substituent selected from cyano and nitro groups, and examples of such substituted alkyl groups are cyanomethyl, cyanoethyl and nitroethyl groups.

The "cycloalkyl group" is a cyclic alkyl group preferably having 3 to 6 carbon atoms, and examples include cyclopropyl, cyclobutyl, cyclopentyl and cyclohexyl groups. These cycloalkyl groups may be substituted by at least one substituent such as a halogen atom or a lower alkyl group.

The "alkenyl group" has a double bond in the molecule, and is preferably a linear or branched alkyl group having 2 to 12 carbon atoms. Specific examples include vinyl, allyl, methallyl, crotyl, prenyl, 3-butenyl, 2-penten-4-yl, 2-hexen-4-yl, 3-methyl-1-buten-4-yl and 2-octen-1-yl. These alkenyl groups may be substituted by at least one substituent selected from halogen atoms, a cyano group and a nitro group. Examples of the substituted alkenyl groups are 1-chloroallyl, 2-chloroallyl, 3-chloroallyl and 2-fluoroallyl groups.

The "alkynyl groups" has a triple bond in the molecule and is preferably a linear or branched alkyl group having 3 to 8 carbon atoms having a triple bond in the molecule. Specific examples of the alkynyl group include propargyl, 1-butyn-3-yl, 1-butyn-4-yl, 2-butyn-4-yl, 2-pentyn-1-yl, and 2-octyn-1-yl groups. These alkyl groups may also be substituted by at least one substituent such as halogen atoms, cyano groups and nitro groups.

The "aralkyl group" preferably have 7 to 12 carbon atoms and includes, for example, benzyl, alpha-phenethyl and beta-phenethyl groups. The aryl moiety (such as phenyl) of the aralkyl group may be substituted by at least 1, preferably 1 to 3, substituents selected from, for example, halogen atoms, lower alkyl groups, lower alkoxy groups, a carboxyl group and a nitro group. Examples of such substituted aralkyl groups include p-methylbenzyl, p-isobutylbenzyl, p-chlorobenzyl, p-fluorobenzyl, p-carboxybenzyl, p-nitrobenzyl and o- or m-substituted products of these.

Examples of the leaving groups are halogen atoms such as fluorine, chlorine, bromine and iodine atoms, a trifluoromethylsulfonyloxy group, a p-tolylsulfonyloxy group, a phenylsulfonyloxy group and a methylsulfonyloxy group, a methoxysulfonyloxy group and an ethoxysulfonyloxy group. Hence, the electrophilic compounds of formula (II) or (III) may include sulfate esters such as dimethyl sulfate or diethyl sulfate.

The process of this invention, as stated above, comprises reacting the aromatic pyruvic acid derivative of general formula (I) with the electrophilic compound of general formula (II) or (III) in the presence of a base in a protic solvent. As a result, (i) the reaction of the aromatic pyruvic acid derivative of general formula (I) with the electrophilic compound of formula (II) gives 2-oxo-3-aromatic carboxylic acid derivative of general formula (IV). When an aromatic pyruvic acid derivative of general formula (I) in which $R^2$ is a hydrogen atom is used as the starting material, a 2-oxo-3-aromatic carboxylic acid derivative of formula (V) can also be produced depending upon the selection of reaction conditions, and (ii) the reaction of the aromatic pyruvic acid derivative of general formula (I) in which $R^2$ is a hydrogen atom with the electrophilic compound of general formula (III) can give the 2-oxo-3-aromatic carboxylic acid derivatives of general formula (VI).

Although there is no intention of limiting the present invention by a reaction mechanism, the reaction mechanism of the present invention is presumed to be that the aromatic pyruvic acid derivative of general formula (I) generates a dianion of the aromatic pyruvic acid when treated with the base in the protic solvent, and then by the reaction with the electrophilic compound of formula (II) or (III), one or two $R^3$ groups are selectively introduced into the 3-position, or cyclization (the introduction of $R^4$ groups) takes place by an intramolecular molecular reaction to give the 2-oxo-3-aromatic carboxylic acid derivatives of general formula (IV), (V) or (VI).

The process of this invention can be schematically shown below.

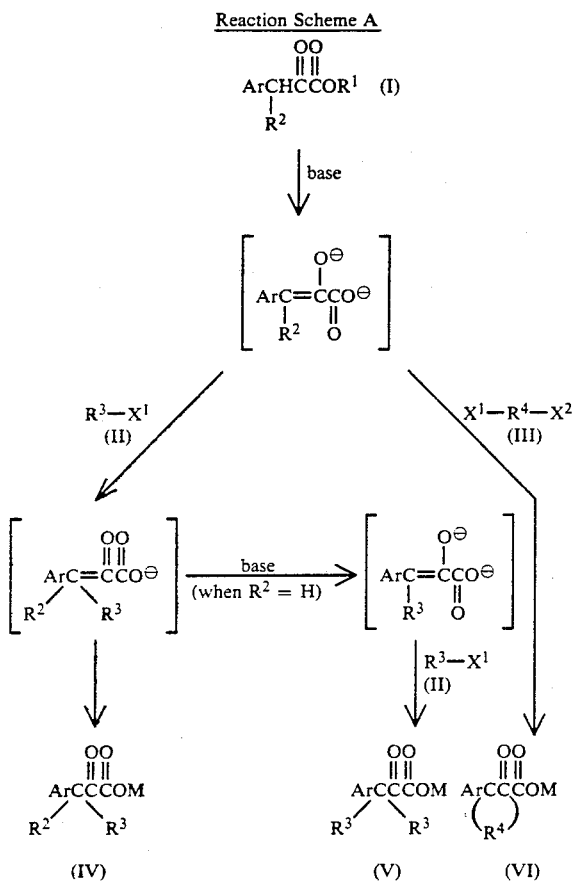

In the above scheme, Ar, $R^1$, $R^2$, $R^3$, $R^4$, $X^1$, $X^2$ and M are as defined hereinabove.

Usually, in a reaction of a carbonyl enolate with an electrophilic reagent, O-alkylation and an aldol condensation type reaction proceed as side-reactions in addition to C-alkylation. In contrast, according to the reaction in accordance with this invention, by utilizing the structural characteristic of the substrate, the aromatic pyruvic acid derivative reacts as a dianion with the electrophilic compound, and the reaction is carried out in the protonic solvent having strong affinity for oxygen atoms. As a result, the above side-reactions are effectively inhibited, and only the C-alkylation is allowed to proceed with good selectivity.

Thus, the reaction of this invention should be carried out in the presence of a base.

Examples of the base that can be used include alkaline metal or alkaline earth metal hydroxides such as sodium hydroxide, potassium hydroxide, lithium hydroxide, calcium hydroxide, and magnesium hydroxide, alkaline metal carbonates such as sodium carbonate and potassium carbonate, and alkali metal alkoxides such as sodium methoxide, sodium ethoxide, potassium methoxide, and potassium-t-butoxide. Among these compounds, sodium hydroxide, potassium hydroxide, lithium hydroxide, calcium hydroxide and sodium methoxide are especially preferably used.

The amount of the base used in the process of this invention is at least one required to form a carboxylate from the standpoint of a chemical reaction, and is an equivalent amount to the electrophilic reagent in view of stoichiometry in reacton with the electrophilic reagent. The amount of the base used, however, differs depending upon the type of the substituents of the starting aromatic pyruvic acid derivative and the electrophilic compound used, and is not always limited to the stoichiometrical amount. The amount of the electrophilic compound also differs depending upon the amount of the base or the reactivity of the electrophilic compound, and is not limited to a stoichiometric amount.

Accordingly, when it is desired to obtain a 2-oxo-3-monosubstituted aromatic carboxylic acid derivative of general formula (IV) selectively, it is preferred to use the electrophilic compound in an amount of not more than 1 equivalent, preferably 0.6 to 1 equivalent, per equivalent of the substrate although it differs depending upon the reaction solvent, or to use the base in an amount of not more than 2 equivalents, especially 1.1 to 2 equivalents. If the formation of the disubstituted compound tends to be inhibited by such factors as the difference of the reactivity of the electrophilic compound or steric hindrance, even the use of more than the stoichiometrical amount of the electrophilic reagent or the base can preferentially give the mono-substituted derivative.

On the other hand, when it is desired to obtain a 2-oxo-3-disubstituted aromatic carboxylic acid derivative of general formula (IV) in which $R^2$ represents the above-defined groups excepting hydrogen, or a 2-oxo-3-disubstituted aromatic carboxylic acid derivative of general formula (V) or (VI), the amounts of the electrophilic compound and the base are not particularly limited, and can be varied over a broad range depending upon the reaction conditions such as the reaction temperature and the type of the solvent. Generally, the use of the electrophilic compound and the base in at least stoichiometrical amounts, preferably 3 to 5 equivalents can give the desired 2-oxo-3-aromatic carboxylic acid derivative in good yields.

When the starting aromatic pyruvic acid derivative and/or the electrophilic compound used has a hydroxyl group, a carboxyl group or a substituent which can have a functional group equivalent thereto under the reaction conditions, for example, at a phenyl ring, these groups form metal salts under the reaction conditions. Accordingly, to obtain the product in good yields, the reaction is preferably carried out in the presence of a base in amounts which are in excess of equivalent amount of the above functional group. This does not apply, however, if a starting material in which these substituents are in the form of a metal salt is used.

If an alkali metal salt or an alkaline earth metal salt where in general formula (1), $R^1$ is an alkali metal or alkaline earth metal) is used as the starting material, the reaction may be carried out while the amount of the corresponding base is decreased.

Another characteristic is that the process of this invention is carried out in a protic solvent, and water, an alcohol solvent and a water-alcohol solvent mixture may be used as the protonic solvent. Examples of the alcohol solvent are methanol, ethanol, isopropyl alcohol, t-butyl alcohol, phenol and catechol. These protic solvents may be used as mixtures with aprotic solvents. Examples of the aprotic solvents that may be used include ether solvents such as tetrahydrofuran, 1,4-dioxane and dimethoxyethane, nitrile solvents such as acetonitrile and propionitrile, ketone solvents such as acetone, methyl ethyl ketone and diethyl ketone, and other aprotic solvents such as N,N-dimethylformamide, dimethyl sulfoxide, sulfolane and hexamethylphosphoric triamide. The amount of the aprotic solvent is usually up to 90 % by volume, preferably 0 to 70 % by volume, of the entire solvent.

The reaction system for this reaction may become a two layer system depending upon the concentration of the base used and the solvent. In this case, if a more hydrophobic electrophilic compound is used, the reaction proceeds slowly, and the desired 2-oxo-3-aromatic carboxylic acid is obtained in a low yield. Accordingly, at least in this case, the present reaction is carried out preferably in the presence of a quarternary ammonium salt. As the quarternary ammonium salt, compounds used in an ordinary phase transfer reaction system may be used likewise. For example, there may be used benzyltriethylammonium chloride, tetraethylammonium chloride, tetrabutylammonium chloride, tetrabutylammonium bromide, tetrabutylammonium iodide, cetyltrimethylammonium chloride and trimethylammonium hydroxide.

When in the reaction of this invention, a electrophilic compound having low reactivity is used, the reaction may be carried out in the presence of an iodide compound such as potassium iodide. As a result, the reaction time can be shortened, and the desired compound can be obtained in a good yield.

The reaction temperature differs depending upon the type of the base and its amount or the type of the solvent. Generally, low temperature of 100° C. or below, preferably 0° to 70° C., at which the starting aromatic pyruvic acid is difficult of undergoing decarboxylation, are convenient.

By performing an operation of isolating the product after the reaction, an alkali metal salt or an alkaline earth metal salt of 2-oxo-3-aromatic carboxylic acid represented by general formula (IV), (V) or (VI) may be obtained. The product may be obtained as a free carboxylic acid by an ordinary treatment. If required, the product can be separated and purified on a silica gel column or by methyl esterifying it with diazomethane to convert it to a carboxylate ester and purify it. The free carboxylic acid may be isolated as a pure sodium salt of the 2-oxo-3-aromatic carboxylic acid by converting the free carboxylic acid into its sodium salt using sodium hydroxide, for example, and subjecting it to a simple separating operation.

The aromatic pyruvic acid derivative of general formula (I) used as the starting material in the process of the invention can be a known compound, or may be prepared by known methods. (See, for example, Japanese Patent Publication No. 18587/1981, and Japanese Laid-Open Patent Publications Nos. 35069/1978, 149970/1978, 4398/1980, 99445/1981, 102825/1984, 61550/1985, 179147/1985, 19650/1986, 19651/1986 and 116541/1987).

BEST MODE OF PRACTICING THE INVENTION

EXAMPLE 1

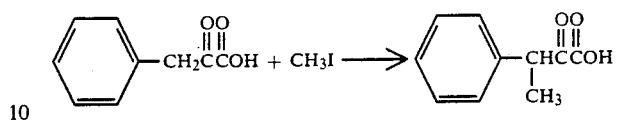

A 1N sodium hydroxide aqueous solution (10 ml; 10 mmoles) was added to 0.82 g (5.0 mmoles) of phenylpyruvic acid to form a solution. Then, 1.0 ml of methyl iodide was added, and the mixture was stirred at room temperature for 9 hours. The reaction mixture was acidified with 1N hydrochloric acid and extracted with 90 ml of ether. The extract was dried over magnesium sulfate, and the ether was concentrated under reduced pressure to give a pale yellowish white solid. It was separated and purified by silica gel column chromatography (ethyl acetate) to give 0.62 g (yield 69 %) of white crystals of 2-oxo-3-phenylbutanoic acid.

$^1$H-NMR spectrum (CDCl$_3$, TMS, ppm): δ1.37(3H, d, J=6.2Hz), 4.53(1H, q, J=6.2Hz), 7.2(5H, s), 8.71(1H, br s).

EXAMPLE 2

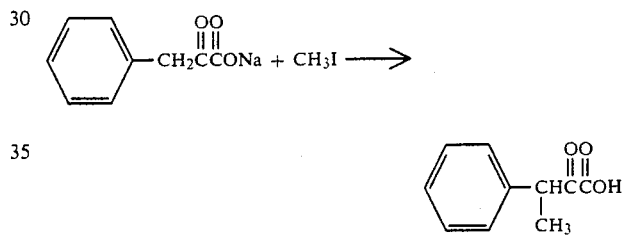

A 1N sodium hydroxide aqueous solution (20 ml, 20 mmoles) and water (20 ml) were added to 3.92 g (20 mmoles) of sodium phenylpuruvate to form a solution. Methyl iodide (1.20 ml) was added, and the mixture was stirred at room temperature for 24 hours. The reaction mixture was acidified with 1N hydrochloric acid, and extracted with 100 ml of ether. The ether layer was dried over magnesium sulfate, and concentrated under reduced pressure to give a pale yellowish white solid. A 2N aqueous solution of sodium hydroxide (9 ml) was added to the solid and concentrated. Ether was added to the resulting semi-solid mixture, and the precipitated sodium 2-oxo-3-phenylbutanoate was isolated as a white solid (3.56 g; yield 89 %) by filtration.

Melting point: 262°–268° C.

$^1$H-NMR spectrum (DMSO-d$_6$, TMS, ppm): δ1.39(3H, d, J=7.2Hz), 4.33(1H, q, J=7.2Hz), 7.25(5H, s).

IR spectrum (KBr, cm$^{-1}$) 1720, 1263.

Elemental analysis values (calculated, C$_{10}$H$_9$O$_3$Na, %): C, 59.71(60.00); H, 4.50(9.07).

EXAMPLE 3

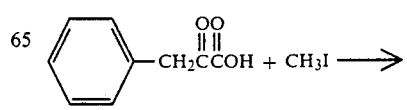

-continued

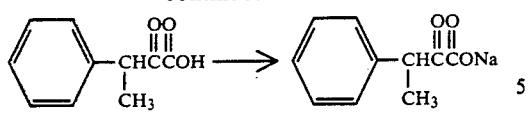

A 1N aqueous solution of sodium hydroxide (20 ml, 20 mmoles) and 40 ml of methanol were added to 1.64 g (10.0 mmoles) of phenylpyruvic acid to form a solution. Then, 2.0 ml of methyl iodide was added, and the mixture was stirred at room temperature for 10 hours. The reaction mixture was acidified with 1N hydrochloric acid, and extracted with 150 ml of ether. The ether layer was dried over magnesium sulfate and concentrated under reduced pressure to give a pale yellowish white solid. To the solid was added 3 ml of a 3N aqueous solution of sodium hydroxide, and the mixture was concentrated under reduced pressure. Ether was added to the resulting semi-solid mixture, and the precipitated sodium 2-oxo-3-phenylbutanoate was isolated as a white solid (1.62 g; yield 81 %) by filtration.

EXAMPLE 4

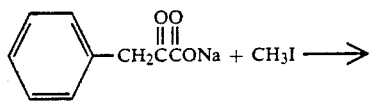

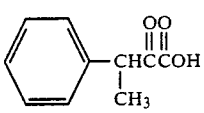

A 2N aqueous solution of sodium hydroxide (10 ml, 20 mmoles) and 30 ml of methanol were added to 3.92 g (20 mmoles) of sodium phenylpyruvate to form a solution. Then, 1.25 ml of methyl iodide was added, and the mixture was stirred at room temperature for 24 hours. The reaction mixture was acidified with 1N hydrochloric acid, and extracted with 150 ml of ether. The ether layer was dried over magnesium sulfate, and concentrated under reduced pressure to give a pale yellowish white oil. A 3N aqueous solution of sodium hydroxide (6.5 ml) was added, and the mixture was concentrated. Ether was added to the resulting semi-solid mixture, and the precipitated sodium 2-oxo-3-phenylbutanoate was isolated by filtration as a white solid (1.62 g, yield 85 %).

EXAMPLE 5

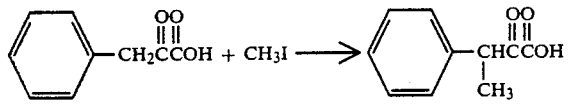

A 3N aqueous solution of sodium hydroxide (3 ml, 9 mmoles) and 6 ml of ethanol were added to 0.492 g (3.0 mmoles) of phenylpyruvic acid to form a solution. Then, 0.6 ml of methyl iodide was added, and the mixture was stirred at room temperature 8 hours. The reaction mixture was acidified with 1N hydrochloric acid, and extracted with 50 ml of ether. The ether layer was dried over magnesium sulfate, and concentrated under reduced pressure to give a pale yellowish white oil. It was determined by its NMR spectrum that 2-oxo-3-phenylbutanoic acid formed in a yield of 69 %. The formation of a very small amount of the corresponding dimethyl compound was detected.

EXAMPLE 6

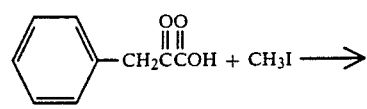

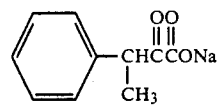

A 1N aqueous solution of sodium hydroxide (20 ml, 20 mmoles) and 30 ml of tetrahydrofuran were added to 1.64 g (10.0 mmoles) of phenylpyruvic acid to form a solution. Then, 2.0 ml of methyl iodide was added, and the mixture was stirred at room temperature for 10 hours. The reaction mixture was concentrated, and ether was added to the resulting pale yellowish white semi-solid. The precipitated sodium 2-oxo-3-phenylbutanoate as a white solid (0.68 g, yield 68 %) was isolated by filtration.

EXAMPLE 7

 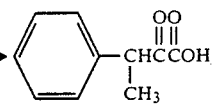

A 1N aqueous solution of sodium hydroxide (10 ml, 10.0 mmoles) and 20 ml of tetrahydrofuran were added to 0.82 g (5.0 mmoles) of phenylpyruvic acid to form a solution. Then, 0.3 ml of methyl iodide was added, and the mixture was stirred for 3.5 hours with water cooling. The reaction mixture was acidified with 1N hydrochloric acid, and extracted with two 100 ml portions of ether. Ether layers were dried over magnesium sulfate and concentrated under reduced pressure to give a pale yellowish white solid. From its NMR spectral analysis, it was determined that 2-oxo-3-phenylbutanoic acid formed almost quantitatively.

EXAMPLE 8

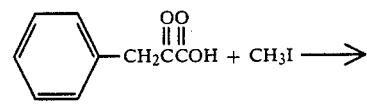

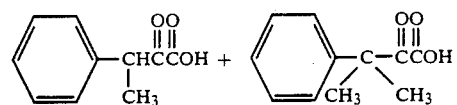

A 1N aqueous solution of sodium hydroxide (20 ml, 20 mmoles) and 30 ml of dimethylformamide were added to 1.64 g (10.0 mmoles) of phenylpyruvic acid to form a solution. Then, 2.0 ml of methyl iodide was added, and the mixture was stirred at room temperature for 10 hours. The reaction mixture was acidified with 1N hydrochloric acid, and extracted with 150 ml of ether. The ether layer was dried over magnesium sulfate, and concentrated under reduced pressure to give a pale yellowish white solid. Analysis of its NMR spectrum showed that 2-oxo-3-phenylbutanoic acid formed in a yield of 59%, and 2-oxo-3-methyl-3-phenylbutanoic acid, in a yield of 21%. The NMR spectrum of the former is shown in Example 1, and that of the latter is shown in Example 73.

EXAMPLE 9

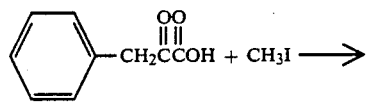

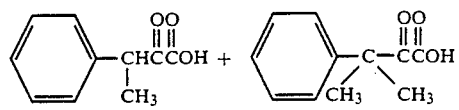

A 3N aqueous solution of sodium hydroxide (3.0 ml, 9.0 mmoles) and 6 ml of t-butyl alcohol were added to 0.492 g (3.0 mmoles) of phenylpyruvic acid to form a solution. Then, 0.6 ml of methyl iodide was added, and the mixture was stirred at room temperature for 9 hours. The reaction mixture was acidified with 20 ml of 1N hydrochloric acid, and extracted with ether. The organic layer was dried over magnesium sulfate. The drying reagent was separated by filtration, and the solvent was evaporated under reduced pressure to give a pale while oil. The NMR spectral analysis of the product led to the determination that 2-oxo-3-phenylbutanoic acid was formed in a yield of 57 %, and 2-oxo-3-methyl-3phenylbutanoic acid, in a yield of 30 %.

EXAMPLE 10

Example 9 was repeated except that 6 ml of 1,4-dioxane was used instead of t-butyl alcohol as the solvent. A mixture of 2-oxo-2-phenylbutanoic acid (70 %) and 2-oxo-3-methyl-3-phenylbutanoic acid (30 %) was obtained.

EXAMPLE 11

Example 9 was repeated except that 6 ml of acetonitrile was used instead of t-butyl alcohol as the solvent. A mixture of 2-oxo-3-phenylbutanoic acid (65 %) and 2-oxo-3-methyl-phenylbutanoic acid (trace) was obtained.

EXAMPLE 12

Example 9 was repeated except that 6 ml of N,N-dimethylformamide was used instead of t-butyl alcohol as the solvent. A mixture of 2-oxo-3-phenylbutanoic acid (39 %) and 2-oxo-3-methyl-3-phenylbutanoic acid (32 %) was obtained.

EXAMPLE 13

Example 9 was repeated except that 6 ml of hexamethylphosphoric triamide was used instead of t-butyl alcohol as the solvent. A mixture of 2-oxo-3-phenylbutanoic acid (46 %) and 2-oxo-3-methyl-3-phenylbutanoic acid (2 %) was obtained.

EXAMPLE 14

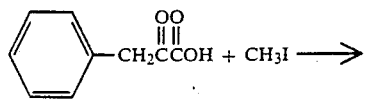

A 2.25N aqueous solution of lithium hydroxide (4.0 ml, 9.0 mmoles) and 6 ml of tetrahydrofuran were added to 0.492 g (3.0 mmoles) of phenylpyruvic acid. The mixture was gradually heated with ice cooling to react it for 12 hours. After the reaction, 20 ml of 1N hydrochloric acid was added, and the mixture was extracted with ether. The organic layer was dried over magnesium sulfate. The drying reagent was separated by filtration, and the solvent was evaporated under reduced pressure to give a pale white solid. The NMR spectral analysis of this product led to the determination that 2-oxo-3-phenylbutanoic acid formed in a yield of 85 %, and 2-oxo-3-methyl-3-phenylbutanoic acid, in a yield of 4 %.

EXAMPLE 15

Example 14 was repeated except that 4.0 ml (9.0 mmoles) of a 2.25N aqueous solution of potassium hydroxide was used instead of lithium hydroxide as a base, and 8 ml of tetrahydrofuran was used as a solvent. A mixture of 2-oxo-3-phenylbutanoic acid (65 %) and 2-oxo-3-methyl-3-phenylbutanoic acid (11 %) was obtained.

EXAMPLE 16

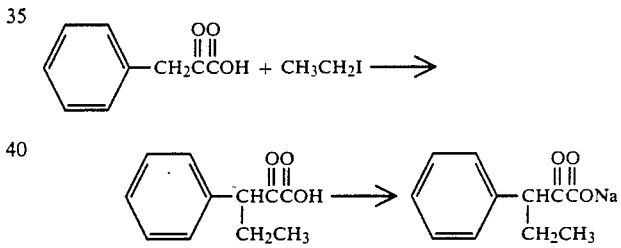

A 3N aqueous solution of sodium hydroxide (7.0 ml, 21 mmoles) was added to 1.64 g (10.0 mmoles) of phenylpyruvic acid to form a solution. Then, 3.0 ml of ethyl iodide was added, and the mixture was stirred at room temperature for 6.5 hours. The reaction mixture was acidified with 1N hydrochloric acid, and extracted with three 30 ml portions of ether. The ether layers were dried over magnesium sulfate, and concentrated under reduced pressure to give a pale yellowish white solid. Its NMR spectral analysis led to the determination that 2-oxo-3-phenylpentanoic acid was formed in a yield of 60%. This product was purified by silica gel column chromatography (ethyl acetate) to give white crystals of pure 2-oxo-3-phenylpentanoic acid.

Melting point: 62°–68° C.

$^1$H-NMR spectrum (CDCl$_3$-DMSO-d$_6$, TMS, ppm): δ0.87(3H, t, J=7.0Hz), 1.93(2H, m), 4.38(1H, q, J=7.0Hz), 7.29(5H, s), 8.97(1H, br s).

An aqueous solution of sodium hydroxide was added to this product, and by the same procedure as in Example 3, the product was isolated as a pure sodium salt.

Melting point: 241°–246° C. IR spectrum (KBr, cm$^{-1}$) 1700, 1630, 1390.

Elemental analysis values (calculated, $C_{11}H_{11}O_3Na \cdot \frac{1}{2} H_2O$, %): C, 59.79(59.19); H, 5.01(5.42).

EXAMPLE 17

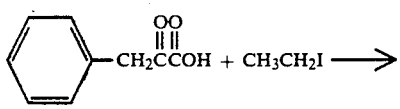

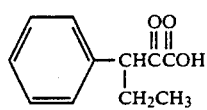

Tetrahydrofuran (20 ml) and a 2N aqueous solution of sodium hydroxide (5.0 ml, 20 mmoles) were added to 1.64 g (10.0 mmoles) of phenylpyruvic acid to form a solution. Then, 1.8 ml of ethyl iodide was added, and the mixture was stirred at room temperature for 7 hours. The reaction mixture was acidified and extracted with three 30 ml portions of ether. The organic layers were dried over magnesium sulfate, and concentrated under reduced pressure to give a pale yellowish white oil. The NMR spectral analysis of this product led to the determination that 2-oxo-3-phenylpentanoic acid was formed in a yield of 65 %.

EXAMPLE 18

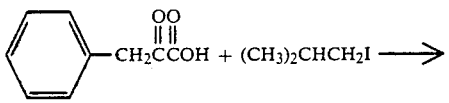

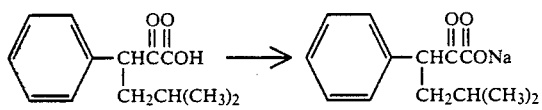

Phenylpyruvic acid (1.64 g, 10 mmoles) was dissolved in 20 ml of methanol. Further, 7.0 ml (21 mmoles) of a 3N aqueous solution of sodium hydroxide and mg of triethylbenzylammonium chloride were added to prepare a solution. Then, 2.0 ml of isobutyl iodide was added, and the mixture was stirred at room temperature for 20 hours. The reaction mixture was acidified with 1N hydrochloric acid, and extracted with three 30 ml portions of ether. The ether layers were dried over magnesium sulfate, and concentrated under reduced pressure to give a pale white oil. Its NMR spectrum led to the determination that 2-oxo-3-phenyl-5-methylhexanoic acid formed in a yield of 28 %.

$^1$H-NMR spectrum (CDCl$_3$-DMSO-d$_6$, ppm): $\delta$0.88(6H, dd, J=2.4Hz), 1.65(3H, m), 4.51(1H, t, J=7.8Hz), 7.26(5H, s), 9.96(1H, br s).

By treating the product with an aqueous solution of sodium hydroxide by the same procedure as in Example 3, it was isolated as a pure sodium salt.

Melting point: 236°–240° C.

IR spectrum (KBr, cm$^{-1}$) 1710, 1650, 1390.

Elemental analysis values (calculated, $C_{13}H_{15}O_3Na \cdot 2/3H_2O$, %) C, 61.54(61.41); H, 6.46(6.48).

EXAMPLE 19

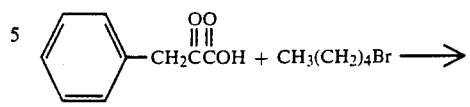

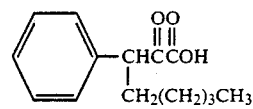

Phenylpyruvic acid (1.64 g, 10-mmoles) was dissolved in 50 ml of methanol, and a 3N aqueous solution of sodium hydroxide and 100 mg of triethylbenzylammonium chloride were added to form a solution. Then, 50 mg of potassium iodide and 2.7 ml of pentyl bromide were added, and the mixture was stirred at 45° C. for 10 hours. The reaction mixture was acidified with 1N hydrochloric acid and extracted with three 50 ml portions of ether. The ether layers were dried over magnesium sulfate and concentrated under reduced pressure to give a pale white oil. Its NMR spectral analysis led to the determination that 2-oxo-3-phenyloctanoic acid formed in a yield of 35%.

$^1$H-NMR spectrum (CDCl$_3$-DMSO-d$_6$, ppm): $\delta$0.57-1.05(3H, m), 0.98-1.50(6H, m), 1.50-2.27(2H, m), 4.50(1H, t, J=7,2Hz), 7.08(5H, s), 8.53(1H, br s).

EXAMPLE 20

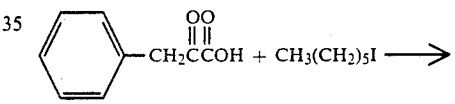

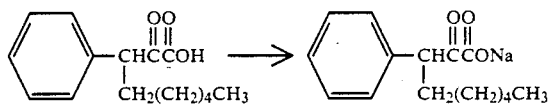

Phenylpyruvic acid (0.49 g, 3.0 mmoles) was dissolved in 6 ml of 1,4-dioxane, and a 3N aqueous solution of sodium hydroxide and 30 ml of triethylbenzylammonium chloride were added to form a solution. Then, 0.6 ml of hexyl iodide was added, and the mixture was stirred at room temperature for 48 hours. The reaction mixture was acidified with 1N hydrochloric acid, and extracted with three 30 ml portions of ether. The ether layers were dried over magnesium sulfate and dried under reduced pressure to give a pale yellowish white oil. Its NMR spectral analysis led to the determination that 2-oxo-3-phenylnonanoic acid was formed in a yield of 29%.

$^1$H-NMR spectrum (CDCl$_3$-DMSO-d$_6$, ppm): $\delta$0.51-1.06(3H, m), 0.95-1.55(8H, m), 1.56-2.35(2H, m), 4.37(1H, t, J=7.2Hz), 7.21(5H, s).

This product was treated with an aqueous solution of sodium hydroxide by the same procedure as in Example 3 to isolate a pure sodium salt.

Melting point: 154°–158° C.

IR spectrum (KBr, cm$^{-1}$) 1690, 1630, 1400.

Elemental analysis values (calculated, $C_{15}H_{19}O_3Na \cdot 2/3H_2O$, %): C, 63.54(63.82); H, 7.25(7.26).

EXAMPLE 21

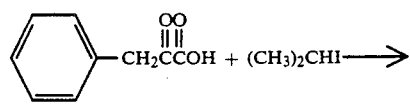

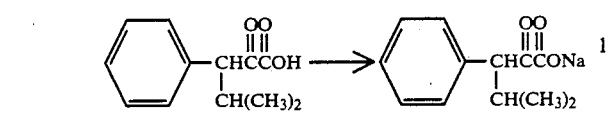

A 1N aqueous solution of sodium hydroxide (10 ml, 10 mmoles) was added to 0.82 g (5.0 mmoles) of phenylpyruvic acid to form a solution. Then, 1.5 ml of isopropyl iodide was added, and the mixture was stirred at room temperature for 36 hours. The reaction mixture was acidified with 1N hydrochloric acid and extracted with three 30 ml portions of ether. The ether layers were dried over magnesium sulfate, and concentrated to give a pale yellowish white solid. Its NMR spectral analysis led to the determination that 2-oxo-3-phenyl-4methylpentanoic acid was formed in a yield of 52 %.

$^1$H-NMR spectrum (CDCl$_3$, TMS, ppm): δ0.71 and 0.97(total 6H, each d, J=6.4Hz), 2.37(1H, m), 4.17(1H, d, J=8.6Hz), 7.31(5H, s), 9.13(1H, br s).

This product was treated with an aqueous solution of sodium hydroxide by the same procedure as in Example 3. It was isolated as a pure sodium salt.

Melting point: 239°–243° C.

IR spectrum (KBr, cm$^{-1}$) 1710, 1630, 1390.

Elemental analysis values (calculated, C$_{12}$H$_{13}$O$_3$-Na•2/3H$_2$O, %): C, 59.72(60.00); H, 5.59(5.73).

EXAMPLE 22

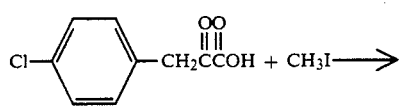

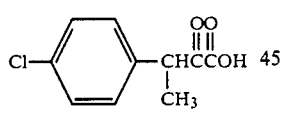

p-Chlorophenylpuruvic acid (0.99 g, 5.0 mmoles) was dissolved in 20 ml of methanol, and a 3N aqueous solution of sodium hydroxide (4.0 ml, 12 mmoles) was added. Then, 2.2 ml of methyl iodide was added, and the mixture was stirred at room temperature for 6 hours. The reaction mixture was acidified with 1N hydrochloric acid, and extracted with three 30 ml portions of ether. The ether layers were dried over magnesium sulfate, and concentrated under reduced pressure to give a pale yellowish solid. Its NMR spectral analysis led to the determination that 2-oxo-3-(p-chlorophenyl)-butanoic acid was formed in a yield of 76 %.

$^1$H-NMR spectrum (CDCl$_3$, TMS, ppm): δ1.46(3H, d, J=7.0Hz), 4.61(1H, q, J=7.0Hz), 7.33(4H, s), 8.67(1H, br s).

The above product was treated with an aqueous solution of sodium hydroxide by the same procedure as in Example 3 to isolate a pure sodium salt.

Melting point: 242°–248° C.

IR spectrum (KBr, cm$^{-1}$) 1715, 1620, 1390.

Elemental analysis values (calculated, C$_{10}$H$_8$ClO$_3$Na, %): C, 51.60(51.19); H, 3.50(3.44).

EXAMPLE 23

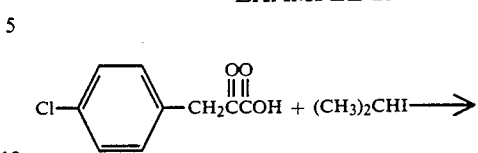

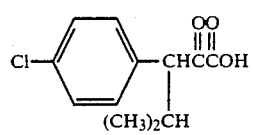

p-Chlorophenylpyruvic acid (1.98 g, 10.0 mmoles) was dissolved in 20 ml of methanol, and further a 3N aqueous solution of sodium hydroxide (7.0 ml, 21 mmoles) was added to form a solution. Then, 100 mg of triethylbenzylammonium chloride and 2.2 ml of isopropyl iodide were added, and the mixture was stirred at room temperature for 20 hours. The reaction mixture was acidified with 1N hydrochloric acid, and extracted with three 30 ml portions of ether. The ether layers were dried over magnesium sulfate, and concentrated under reduced pressure to give a pale yellowish white solid. Its NMR spectral analysis led to the determination that 2-oxo-3-(p-chlorophenyl)-methylpentanoic acid was formed in a yield of 25 %.

$^1$H-NMR spectrum (CDCl$_3$-DMSO-d$_6$, TMS, ppm): δ0.70 and 1.13(total 6H, each d, J=4.0Hz), 2.40(1H, m), 4.14(1H, d, J=6.6Hz), 7.37(4H, s).

EXAMPLE 24

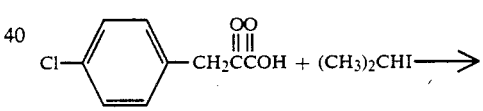

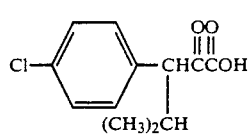

p-Chlorophenylpyruvic acid (1.98 g, 10.0 mmoles) was dissolved in 20 ml of methanol, and a 3N aqueous solution of sodium hydroxide (8.0 ml, 24 mmoles) was added to form a solution. Then, 2.0 ml of isopropyl iodide was added, and the mixture was stirred at 35° C. for 36 hours. The reaction mixture was acidified with 1N hydrochloric acid and extracted with three 30 ml portions of ether. The ether layers were dried over magnesium sulfate and concentrated under reduced pressure. The resulting pale yellowish white oil was purified by silica gel column chromatography (ethyl acetate:hexane=1:7) to obtain pure 2-oxo-3-(p-chlorophenyl)-4-methylpentanoic acid as an oil in a yield of 48 %. This product was treated with an aqueous solution of sodium hydroxide, and isolated as a pure sodium salt.

Melting point: 220°–224° C.

IR spectrum (KBr, cm$^{-1}$) 1710, 1640, 1390.

EXAMPLE 25

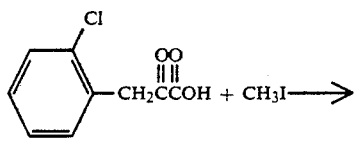

o-Chlorophenylpyruvic acid (10 g, 50.4 mmoles), 125 ml of a 2.4N aqueous solution of sodium hydroxide and 50 ml of tetrahydrofuran were added and stirred until the mixture completely became uniform. Then, 45 g (362.8 mmoles) of methyl iodide and 0.1 g of tetramethylammonium bromide were added, and reacted at room temperature for 48 hours. The reaction mixture was acidified with 1N hydrochloric acid and extracted with two 150 ml portions of ether. The organic layers were washed with an aqueous saturated solution of sodium thiosulfate. Then, the ether layer was washed with water and dried over magnesium sulfate. The drying reagent was separated by filtration, and the solvent was evaporated. The NMR spectral analysis of the resulting oil led to the determination that 2-oxo-4-(o-chlorophenyl)butanoic acid was formed in a yield of 80 %, and 2-oxo-3-methyl-3-(o-chlorophenyl)butanoic acid, in a yield of 20 %. The NMR spectra of these products are shown below.

2-oxo-3-(o-chlorophenyl)butanoic acid
$^1$H-NMR (CDCl$_3$, TMS, ppm): δ1.45(3H, d, J=7Hz), 4.97(1H, q, J=7Hz), 7.02–7.49(4H, m), 9.28(1H, s).

2-oxo-3-methyl-3-(o-chlorophenyl)butanoic acid
$^1$H-NMR (CDCl$_3$, TMS, ppm): δ1.65(6H, s), 7.02–7.49(4H, m), 9.28(1H, s).

EXAMPLE 26

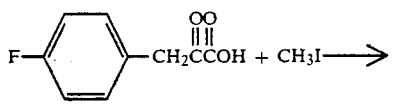

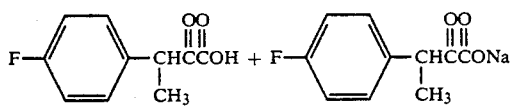

A 3N aqueous solution of sodium hydroxide (5.0 ml, 15 mmoles) and 20 ml of methanol were added to p-fluorophenylpyruvic acid (0.92 g, 5.0 mmoles) to form a solution. Then, 2.0 ml of methyl iodide was added, and the mixture was stirred at room temperature for 14 hours. The reaction mixture was acidified with 1N hydrochloric acid, and extracted with three 30 ml portions of ether. The ether layers were dried over magnesium sulfate, and concentrated under reduced pressure to give a pale yellowish white solid. To the product was added 2 ml of a 3N aqueous solution of sodium hydroxide, and the mixture was concentrated under reduced pressure. Ether was added to the resulting semi-solid mixture, and the precipitated sodium 2-oxo-3-(p-fluoro-phenyl)butanoate was isolated by filtration as a white solid (yield 26 %).

Melting point: 240°–249° C.
$^1$H-NMR spectrum (DMSO-d$_6$, TMS, ppm): δ1.14(3H, d, J=7.0Hz), 4.53(1H, q, J=7.0Hz), 6.9–7.3(4H, m), 8.72(1H, br s).
IR spectrum (KBr, cm$^{-1}$) 1710, 1615, 1385.
Elemental analysis values (calculated, C$_{10}$H$_8$FO$_3$Na, %): C, 54.90(55.06); H, 3.61(3.70).

EXAMPLE 27

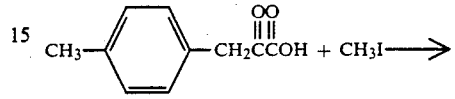

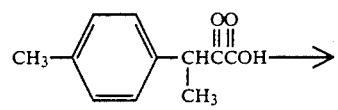

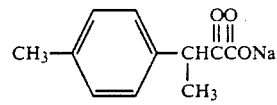

A 3N aqueous solution of sodium hydroxide (4.0 ml, 12 mmoles) and 10 ml of methanol were added to 0.53 g (3.0 mmoles) of p-methylphenylpyruvic acid to form a solution. Then, 1.0 ml of methyl iodide was added, and the mixture was stirred at room temperature for 4.5 hours. The reaction mixture was acidified with 1N hydrochloric acid and extracted with three 30 ml portions of ether. The ether layers were dried over magnesium sulfate, and concentrated under reduced pressure to give a pale brown oil. Its NMR spectral analysis led to the determination that 2-oxo-3-(p-methylphenyl)-butanoic acid was formed in a yield of 80 %. To this product was added 3 ml of a 3N aqueous solution of sodium hydroxide, and the mixture was concentrated under reduced pressure. Ether was added to the resulting semi-solid mixture, and the precipitated sodium 2-oxo-3-(p-methylphenyl)butanoate was isolated by filtration as a white solid.

Melting point: 252°–256° C.
$^1$H-NMR spectrum (CDCl$_3$-DMSO-d$_6$, TMS, ppm): δ1.41(3H, d, J=6.8Hz), 2.26(3H, s), 4.51(1H, q, J=6.8Hz), 7.11(4H, s), 7.75(1H, br s).
IR spectrum (KBr, cm$^{-1}$) 1715, 1620, 1390.
Elemental analysis values (calculated, C$_{11}$H$_{11}$O$_3$Na, %): C, 61.56(61.68); H, 5.16(5.18).

EXAMPLE 28

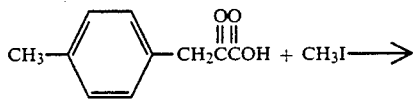

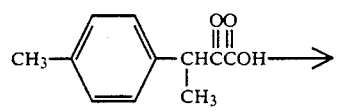

-continued

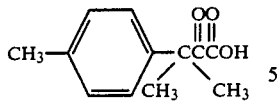

A 3N aqueous solution of sodium hydroxide (8.43 ml) and 10 ml of tetrahydrofuran were added to 1.50 g (8.4 mmoles) of p-methylphenylpyruvic acid, and the mixture was stirred until it became completely uniform. Then, 2.1 ml (34 mmoles) of methyl iodide was added, and the mixture reacted at room temperature for 12 hours. The reaction mixture was acidified with 1N hydrochloric acid and extracted with ether. The extract was dried over magnesium sulfate. The drying reagent was separated by filtration, and the solvent was evaporated. The NMR spectral analysis of the resulting oily product led to the determination that 2-oxo-3-(p-methylphenyl)butanoic acid and 2-oxo-3-methyl-3-(p-methylphenyl)butanoic acid were formed in a yield of 58 % and 42 %, respectively. The NMR spectrum of the former is shown in Example 27, and that of the latter compound, in Example 77.

EXAMPLE 29

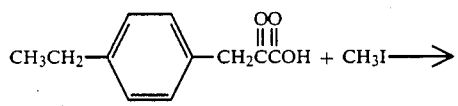

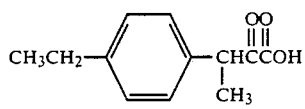

A 3N aqueous solution of sodium hydroxide (2.0 ml; 6.0 mmoles) and 6.0 ml of methanol were added to 0.57 g (3.0 mmoles) of p-ethylphenylpyruvic acid to form a solution. Then, 0.5 ml of methyl iodide was added, and the mixture was stirred at room temperature for 4 hours. The reaction mixture was acidified by adding 1N hydrochloric acid and extracted with three 30 ml portions of ether. The ether layers were dried over magnesium sulfate, and concentrated under reduced pressure to give a pale yellow solid. It was determined by its NMR spectrum analysis that this solid was nearly pure 2-oxo-3-(p-ethylphenyl)butanoic acid. The yield was 93 %.

$^1$H-NMR spectrum (CDCl$_3$, TMS, ppm): δ1.17(3H, t, J=7.2Hz), 1.40(3H, d, J=7.0Hz), 2.58(2H, q, J=7.2Hz), 4.49(1H, q, J=7.0Hz), 7.11(4H, s), 9.97(1H, br s).

EXAMPLE 30

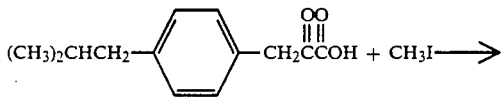

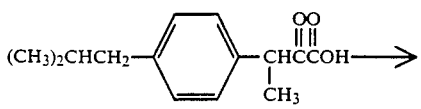

-continued

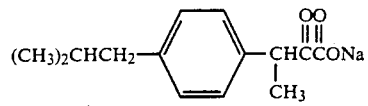

Methanol (25 ml) was added to 2.20 g (10 mmoles) of p-isobutylphenylpyruvic acid to dissolve it completely. With ice cooling, a 3N aqueous solution of sodium hydroxide (7 ml; 21.0 mmoles) was added. Then, 2.0 ml of methyl iodide was added, and the mixture was stirred at room temperature for 13 hours. The reaction mixture was acidified by adding 1N hydrochloric acid and extracted with 90 ml of ether. The ether layer was dried over magnesium sulfate and the ether was evaporated under reduced pressure to give a pale red oil. The NMR spectral analysis of this product led to the determination that this product was nearly pure 2-oxo-3-(p-isobutylphenyl)butanoic acid. A 3N aqueous solution of sodium hydroxide (4.0 ml) was added to this product, and the mixture was concentrated under reduced pressure. Ether was added to the resulting pale yellowish white solid. By filtration, 1.87 g (yield 76 %) of sodium 2-oxo-3-(p-isobutylphenyl)butanoate was isolated.

Melting point: more than 300° C.

$^1$H-NMR spectrum (DMSO-d$_6$, TMS, ppm): δ0.87(6H, d, J=7.5Hz), 1.32(3H, d, J=7.2Hz), 1.82(1H, desp, J=6.9 and 7.5Hz), 2.40(2H, d, J=6.9Hz), 4.12(1H, q, J=7.2Hz), 7.10(4H, s).

IR spectrum (KBr, cm$^{-1}$) 1710, 1615, 1390.

Elemental analysis values (calculated, C$_{14}$H$_{17}$O$_3$Na.1/3H$_2$O, %): C, 64.44(64.11); H, 6.69(6.79).

EXAMPLE 31

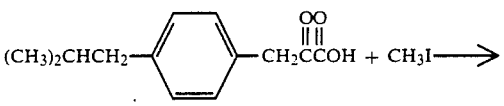

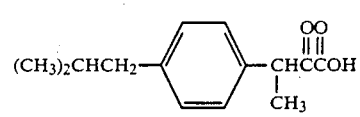

A 3N aqueous solution of sodium hydroxide (20 ml; 60 mmoles) was slowly added to a solution of 6.60 g (30 mmoles) of p-isobutylphenylpyruvic acid and 10 ml of methyl iodide. After the addition, the mixture was stirred at room temperature for 4 hours, acidified with 1N hydrochloric acid, and extracted with 150 ml of ether. The ether layer was dried over magnesium sulfate, and the ether was evaporated under reduced pressure to give pale yellowish white crystals. The NMR spectrum of the crystals led to the determination that the crystals were nearly pure 2-oxo-3-(p-isobutylphenyl)butanoic acid (4.67 g; yield 67 %).

$^1$H-NMR spectrum (CDCl$_3$, TMS, ppm): δ0.87(6H, d, J=7.5Hz), 1.45(3H, d, J=6.6Hz), 1.82(1H, desp, J=6.9 and 7.5Hz), 2.40(2H, d, J=6.9Hz), 4.58(1H, q, J=6.6Hz), 7.10(4H, s).

EXAMPLE 32

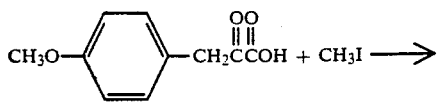

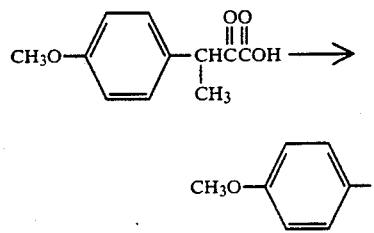

A 1N aqueous solution of sodium hydroxide (20 ml; 20 mmoles) was slowly added to 1.94 g (10 mmoles) of p-methoxyphenylpyruvic acid and a solution of 1.0 ml of methyl iodide in 50 m 1 of methanol. After addition, the mixture was stirred at room temperature for 4 hours. The mixture was acidified with 1N hydrochloric acid and extracted with three 30 ml portions of ether. The ether layers were dried over magnesium sulfate, and the ether was evaporated under reduced pressure to give a pale yellowish white solid. The NMR spectral analysis of this product led to the determination that this product was nearly pure 2-oxo-3-(p-methoxyphenyl)-butanoic acid (1.40 g; yield 67 %).

$^1$H-NMR spectrum (CDCl$_3$, TMS, ppm): δ1.47(3H, d, J=7.5Hz), 3.78(3H, s), 4.60(1H, q, J=7.5Hz), 6.82(2H, d, J=9.0Hz), 7.17(2H, d, J=9.1 Hz), 8.47(1H, br s).

This product was isolated as a pure sodium salt by using an aqueous solution of sodium hydroxide by the same procedure as in Example 3.

Melting point: more than 300° C.
IR spectrum (KBr, cm$^{-1}$) 1710, 1660, 1615.
Elemental analysis values (calculated, C$_{11}$H$_{11}$O$_4$-Na•1/3H$_2$O, %): C, 56.20(55.94); H, 4.78(4.83).

EXAMPLE 33

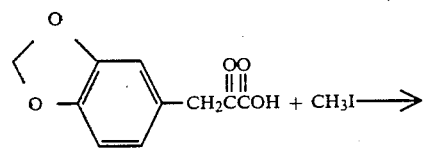

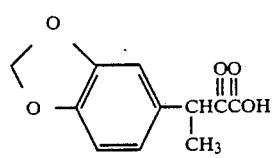

Methanol (10 ml) and 4.0 ml (12 mmoles) of a 3N aqueous solution of sodium hydroxide were added to 1.11 g (5.0 mmoles) of 3,4-methylenedioxyphenyl-pyruvic acid to prepare a solution. Methyl iodide (2.0 ml) was added, and the mixture was stirred at room temperature for 4 hours. After the reaction, the reaction mixture was acidified with 1N hydrochloric acid, and extracted with three 30 ml portions of ether. The ether layers were dried over magnesium sulfate, and the ether was evaporated under reduced pressure to give a red oily product. The NMR spectral analysis of this product led to the determination that 2-oxo-3-(3,4-methylenedioxyphenyl)butanoic acid formed in a yield of 75 %.

$^1$H-NMR spectrum (CDCl$_3$, TMS, ppm): δ1.45(3H, d, J=7.2Hz), 4.54(1H, q, J=7.2Hz), 2.95(2H, s), 6.75(3H, s), 8.67(1H, br s).

EXAMPLE 34

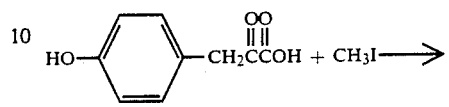

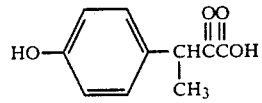

Tetrahydrofuran (6 ml) and 3.0 ml (6 mmoles) of a 2N aqueous solution of sodium hydroxide were added to 0.36 g (2 mmoles) of p-hydroxyphenylpyruvic acid to form a solution. Then, 1.6 ml of methyl iodide was added, and the mixture was stirred at room temperature for 9 hours. After the reaction, the reaction mixture was acidified with 1N hydrochloric acid and extracted with three 30 ml portions of ether. The ether layers were dried over magnesium sulfate, and the ether was evaporated under reduced pressure to give a pale yellowish white oil. The NMR spectral analysis of the oil led to the determination that 2-oxo-3-(p-hydroxyphenyl)-butanoic acid formed in a yield of 31 %.

$^1$H-NMR spectrum (CDCl$_3$, TMS, ppm): δ1.42(3H, d, J=6.8Hz), 4.33(1H, q, J=6.8Hz), 6.74(2H, d, J=8.4Hz), 6.96(2H, d, J=8.4Hz), 10.00(1H, br s).

EXAMPLE 35

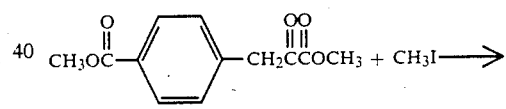

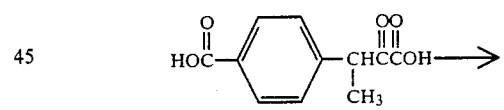

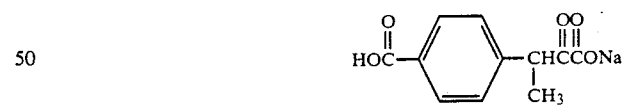

A 3N aqueous solution of sodium hydroxide (20 ml; 60 mmoles) was added to 4.82 g (20 mmoles) of methyl p-methoxycarbonylphenylpyruvate, and the mixture was stirred at room temperature for 30 minutes. Then, 50 ml of tetrahydrofuran and 3.0 ml of methyl iodide were added, and the mixture was reacted at room temperature for 12 hours. After the reaction, the reaction mixture was acidified with 1N of hydrochloric acid, and extracted with ethyl acetate. The organic layer was dried over anhydrous magnesium sulfate, and concentrated under reduced pressure to give a yellowish white solid of 2-oxo-3-(p-hydroxycarbonylphenyl)butanoic acid. 3N sodium hydroxide (5.5 ml) was added to the resulting solid, and the mixture was concentrated under reduced pressure, and then ether was added. Sodium 2-oxo-3-(p-hydroxycarbonylphenyl)butanoate (4.18 g; yield 88 %) which precipitated was isolated by filtration.

Melting point: more than 300° C.

$^1$H-NMR spectrum (CDCl$_3$-DMSO-d$_6$, TMS, ppm): δ1 52(3H, d, J=7.0Hz), 4.67(1H, q, J=7.0Hz), 7.39(2H, d, J=8.0Hz), 8.06(2H, d, J=8.0Hz), 10.39(1H, br s).

IR spectrum (KBr, cm$^{-1}$) 1710, 1680, 1410.

Elemental analysis values (calculated, C$_{11}$H$_9$O$_5$Na, %): C, 54.21(54.11); H, 3.89(3.72).

EXAMPLE 36

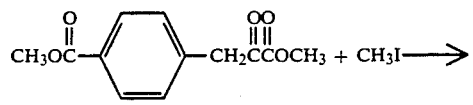

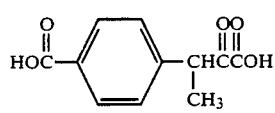

A 2N aqueous solution of sodium hydroxide (15 ml; 30 mmoles) and 5 ml of water were added at room temperature to 2.32 g (10 mmoles) of methyl p-methoxycarbonylphenylpyruvate, and the mixture was stirred at room temperature for 30 minutes. Then, 30 ml of 1,4dioxane and 0.75 ml of methyl iodide were added, and the mixture was reacted at room temperature for 12 hours. After the reaction, the reaction mixture was acidified with 1N hydrochloric acid, and extracted with ethyl acetate. The organic layer was dried over anhydrous magnesium sulfate, and concentrated under reduced pressure to give 1.98 g of a whitish yellow solid. The NMR spectral analysis of this product led to the determination that nearly pure 2-oxo-3-(p-hydroxycarbonylphenyl)butanoic acid formed in a yield of 87 %.

$^1$H-NMR spectrum (CDCl$_3$-DMSO-d$_6$, TMS, ppm): δ1.52(3H, d, J=7.0Hz), 4.67(1H, q, J=7.0Hz), 7.39(2H, d, J=8.0Hz), 8.06(2H, d, J=8.0Hz), 10.39(1H, br s).

EXAMPLE 37

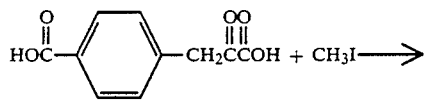

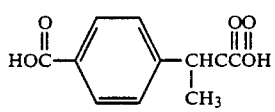

A 3N aqueous solution of sodium hydroxide (10 ml; 30 mmoles) and 50 ml of water were added to 2.08 g (10 mmoles) of p-hydroxycarbonylphenylpyruvic acid. Then 1.0 ml of methyl iodide was added, and the mixture reacted at room temperature for 10 hours. After the reaction, the reaction mixture was acidified with 100 ml of 1N hydrochloric acid and extracted with ethyl acetate. The organic layer was dried over anhydrous magnesium sulfate, and concentrated under reduced pressure to give a whitish yellow solid (1.89 g). The NMR spectral analysis of this solid led to the determination that nearly pure 2-oxo-3-(p-hydroxycarbonylphenyl)-butanoic acid formed in a yield of 85 %.

EXAMPLE 38

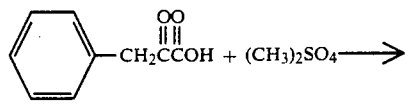

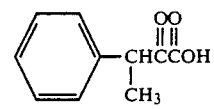

A 2N aqueous solution of sodium hydroxide (5.0 ml; 10 mmoles) was added to 0.82 g (5.0 mmoles) of phenylpyruvic acid to form a solution. Then, 0.5 ml of dimethyl sulfate was added, and the mixture was stirred at room temperature for 7.5 hours. The reaction mixture was acidified with 1N hydrochloric acid, and extracted with 50 ml of ether. The organic layer was dried over magnesium sulfate and concentrated under reduced pressure to give a pale yellowish white solid. The NMR spectral analysis of the solid led to the determination that 2-oxo-3-phenylbutanoate formed in a yield of 55 %.

EXAMPLE 39

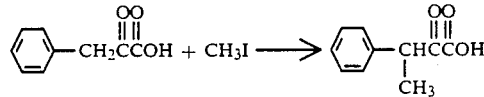

Potassium carbonate (1.5 g), 20 ml of N,N-dimethylformamide and 2 ml of hexamethylphosphoric triamide were put in 1.64 g (10 mmoles) of phenylpyruvic acid, and the mixture was stirred at room temperature for 19 hours. Subsequently, 1.5 ml of methyl iodide was added, and the mixture was stirred for 6 hours. The reaction mixture was extracted with ether. The ether layer washed with water (60 ml), and dried over magnesium sulfate. The drying agent was removed, and the solvent was concentrated under reduced pressure to give 1.26 g of an oily product. The NMR spectral analysis of the product led to the determination that 2-oxo-3-phenylbutanoic acid formed in a yield of 30 %.

EXAMPLE 40

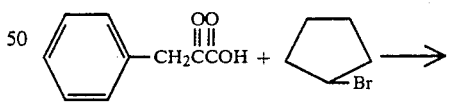

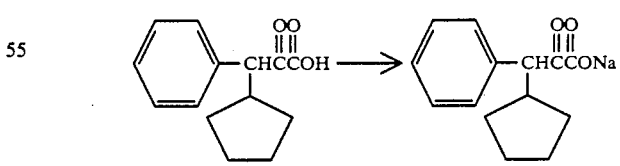

Phenylpyruvic acid (1.64 g; 10.0 mmoles) was dissolved in 20 ml of methanol, and 8 ml (24 mmoles) of a 3N aqueous solution of sodium hydroxide, 80 ml of potassium iodide and 100 mg of triethylbenzylammonium chloride were added. Then, 2.0 ml of cyclopentyl bromide was added, and the mixture was stirred at 37° C. for 24 hours. The reaction mixture was acidified with 1N hydrochloric acid, and extracted with 100 ml of ether. The ether layer was dried over magnesium sulfate, and concentrated under reduced pressure to give a pale yellowish white oil. The NMR spectral analysis of this product led to the determination that 2-oxo-3-cyclopentyl-3phenylpropionic acid formed in a yield of 60 %.

$^1$H-NMR spectrum (CDCl$_3$, TMS, ppm): δ1.60(8H, m), 2.55(1H, m), 4.35(1H, d, J=10.5Hz), 7.28(5H, s).

Then, 3 ml of a 2N aqueous solution of sodium hydroxide was added, and the mixture was concentrated under reduced pressure. Ether was added, and a white solid that precipitated was isolated by filtration to give 1.49 g (5.88 mmoles) of sodium 2-oxo-3-cyclopentyl-3-phenylpropionate in a yield of 59 %.

Melting point: 190°-195° C. or higher.

$^1$H-NMR spectrum (CDCl$_3$-DMSO-d$_6$, ppm): δ1.53(8H, m), 2.48(1H, m), 4.47(1H, d, J=10.5Hz), 7.23(5H, s).

IR spectrum (KBr, cm$^{-1}$) 1700, 1630, 1390.

Elemental analysis values (calculated, C$_{14}$H$_{15}$O$_3$·Na•½H$_2$O, %): C, 63.13(63.87); H, 5.59(6.12).

EXAMPLE 41

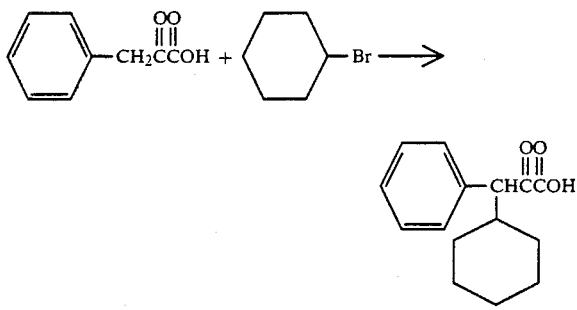

Phenylpyruvic acid (0.82 g; 5.0 mmoles) was dissolved in 10 ml of tetrahydrofuran, and 2 ml (38 mmoles) of a 40 % aqueous solution of sodium hydroxide, 2 ml of water, 50 mg of potassium iodide and 50 mg of triethylbenzylammonium chloride were added. Then, 0.9 ml of cyclohexyl bromide was added, and the mixture was stirred at room temperature for 48 hours. The reaction mixture was acidified with 1N hydrochloric acid and extracted with 50 ml of ether. The ether layer was dried over magnesium sulfate, and then concentrated under reduced pressure to give a pale yellowish white oil. The NMR spectral analysis of this product led to the determination that 2-oxo-3-cyclohexyl-3-phenylpropionic acid formed in a yield of 19 %.

$^1$H-NMR spectrum (CDCl$_3$-DMSO-d$_6$, ppm): δ0.64-2.11(10H, m), 2.47(1H, m), 4.21(1H, d, J=10.8Hz), 7.18(5H, s).

EXAMPLE 42

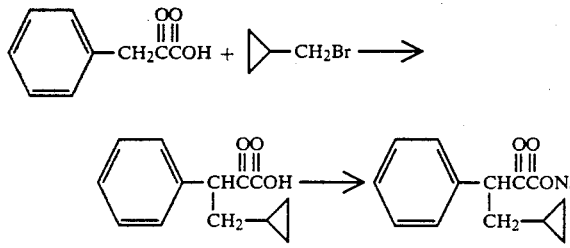

A 3N aqueous solution of sodium hydroxide (4 ml), 10 ml of tetrahydrofuran, 50 mg of potassium iodide and 50 mg of triethylbenzylammonium chloride were added to 0.82 g (5 mmoles) of phenylpyruvic acid. Then, 1.0 ml of bromomethylcyclopropane was added, and the mixture was stirred at room temperature for 16 hours. The reaction mixture was acidified with 1N hydrochloric acid, and extracted with three 30 ml portions of ether. The ether layers were dried over magnesium sulfate, and then concentrated under reduced pressure to give a pale yellowish white oil. This product was esterified with diazomethane to form the methyl ester, and the methyl ester was isolated and purified by silica gel column chromatography (ethyl acetate:hexane=1:12). The NMR spectrum analysis of this product led to the determination that 4-cyclopropyl-3-phenylbutanoic acid formed in a yield of 64 %.

$^1$H-NMR spectrum (CDCl$_3$, TMS, ppm): δ0.26-0.80(5H, m), 1.83(2H, dd, J=7.0Hz), 4.62(1H, t, J=7.0Hz), 7.25(5H, s), 9.07(1H, br s).

A 1N aqueous solution of sodium hydroxide (3.2 ml) was added to the resulting product, and the mixture was concentrated under reduced pressure. Ether was added to the resulting semi-solid mixture. The resulting sodium 4-cyclopropyl-3-phenylbutanoate precipitated as a white solid (yield 62 %) was isolated by filtration.

Melting point: 180°-185° C.

$^1$H-NMR spectrum (DMSO-d$_6$, ppm): δ0.23-0.70(5H, m), 1.30-2.03(2H, dd, J=7.0Hz), 7.26(5H, s).

IR spectrum (KBr, cm$^{-1}$) 1700, 1625, 1395.

Elemental analysis values (calculated, C$_{13}$H$_{13}$O$_3$·Na•H$_2$O, %): C, 62.05(62.65); H, 5.54(5.67).

EXAMPLE 43

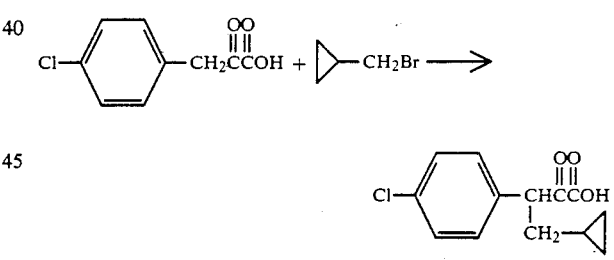

A 3N aqueous solution of sodium hydroxide (7 ml), 20 ml of tetrahydrofuran, 100 mg of potassium iodide and 000 mg of triethylbenzylammonium chloride were added to 1.64 g (10 mmoles) of p-chlorophenylpyruvic acid to form a solution. Then, 1.2 ml of bromomethylcyclopropane was added, and the mixture was stirred at room temperature for 15 hours. The reaction mixture was acidified with 1N hydrochloric acid, and extracted with 100 ml of ether. The ether layer was dried over magnesium sulfate, and concentrated under reduced pressure to give an oily product. The NMR spectral analysis of this product led to the determination that 4-cyclopropyl-3-(p-chlorophenyl)butanoic acid formed in a yield of 60 %.

$^1$H-NMR spectrum (CDCl$_3$, TMS, ppm): δ0.15-0.28(2H, m), 0.28-2.35(3H, m), 1.85(2H, dd, J=7.0Hz), 4.57(1H, t, J=7.0Hz), 7.55(5H, s), 9.13(1H, br s).

EXAMPLE 44

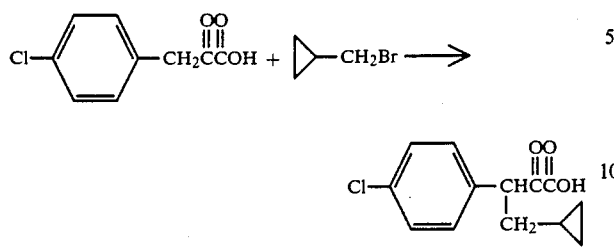

A 3N aqueous solution of sodium hydroxide (4 ml), 10 ml of 1,4-dioxane, 50 mg of potassium iodide and 50 mg of triethylbenzylammonium chloride were added to 0.99 g (5 mmole) of p-chlorophenylpyruvic acid to form a solution. Then, 0.6 ml of bromomethylcyclopropane was added, and the mixture was stirred at room temperature for 15 hours. The reaction mixture was acidified with 1N hydrochloric acid and extracted with 100 ml of ether. The ether layer was dried over magnesium sulfate, and concentrated under reduced pressure to give an oily product. The NMR spectral analysis of this product led to the determination that 4-cyclopropyl-3-(p-chlorophenyl)butanoic acid formed in a yield of 80 %. A 2N aqueous solution of sodium hydroxide (2.0 ml) was added to the product, and the mixture was concentrated under reduced pressure. Ether was added to the resulting semi-solid mixture, and sodium 4-cyclopropyl-3-(p-chlorophenyl)butanoate precipitated as a white solid (yield 64 %) was isolated by filtration.

Melting point: 175°–178° C.
IR spectrum (KBr, cm$^{-1}$) 1710, 1615, 1390.

EXAMPLE 45

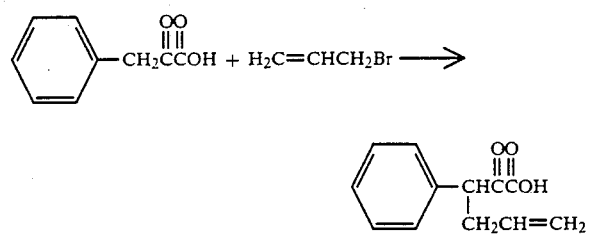

A 1N aqueous solution of sodium hydroxide (20 ml; 20 mmoles) was added to 1.64 g (10 mmoles) of phenylpyruvic acid to form a solution. Then, 1.21 g (10 mmoles) of allylbromide was added, and the mixture was stirred at room temperature for 13 hours. The reaction mixture was acidified with 1N hydrochloric acid and extracted with three 10 ml portions of ethyl acetate. The organic layers were dried over magnesium sulfate, and the ether was evaporated under reduced pressure to give a pale yellow solid. Its NMR spectral analysis led to the determination that this product was nearly pure 2-oxo-phenyl-5-hexenoic acid (1.94 g; yield 95 %).

Melting point: 59°–66° C.
$^1$H-NMR spectrum (CDCl$_3$, ppm): δ2.48(1H, m), 2.78(1H, m), 4.51(1H, t, J=6.9Hz), 4.94(1H, tdd, J=2.1, 1,2, and 1.6Hz), 4.99(1H, tdd, J=1.6, 1.2, and 9.6Hz), 5.68(1H, ddt, J=1.6, 9.6, and 6.6Hz), 7.25(5H, s).
IR spectrum (KBr, cm$^{-1}$) 1730, 1705, 1240.
Elemental analysis values (calculated, C$_{12}$H$_{12}$O$_3$, %): C, 70.69(70.58); H, 5.86(5.92).

EXAMPLE 46

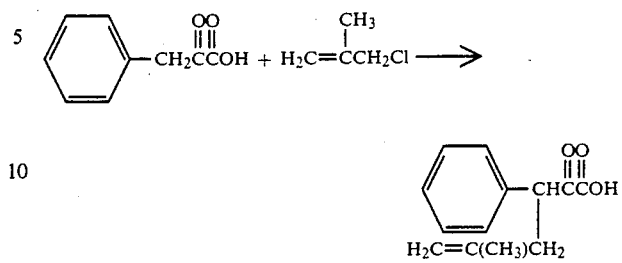

By the same procedure as in Example 45, 2-oxo-phenyl-5-methyl-5-hexenoic acid (yield 52 %) was obtained from 1.64 g (10 mmoles) of phenylpyruvic acid and 1.35 (10 mmoles) of methallyl chloride using a 1N aqueous solution of sodium hydroxide (20 ml; 20 mmoles).

$^1$H-NMR spectrum (CDCl$_3$, ppm): δ1.68(3H, br s), 2.45 (1H, dd, J=14.7 and 7.5 Hz), 2.88(1H, dd, J=14.7 and 7.5Hz), 4.60(1H, m), 4.69(1H, m), 4.72(1H, t, J=6.9Hz), 7.25(5H, s), 8.71(1H, br).

EXAMPLE 47

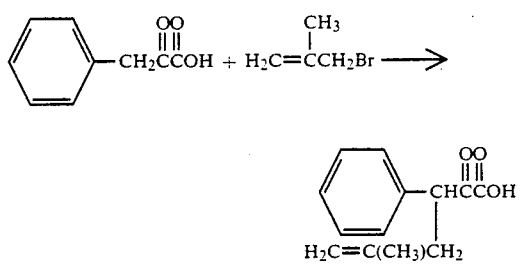

A 1N aqueous solution of sodium hydroxide (20 ml; 20 mmoles) was added to 1.64 g (10 mmoles) of phenylpyruvic acid to form a solution. Then, 1.21 g (10 mmoles) of methallyl bromide was added, and the mixture was stirred at room temperature for 13 hours. The reaction mixture was acidified with 1N hydrochloric acid, and extracted with three 10 ml portions of ethyl acetate. The organic layers were dried over magnesium sulfate, and the ether was evaporated under reduced pressure to give a pale brown oil. The NMR spectral analysis of this product led to the determination that it was nearly pure 2-oxo-3-phenyl-4-methyl-5-hexenoic acid (yield 52 %).

$^1$H-NMR spectrum (CDCl$_3$, ppm): δ1.50 and 1.58(total 3H, each br s), 2.41(1H, m), 2.79(1H, m), 4.45(1H, t, J=6.9Hz), 4.94(1H, m), 7.21(5H, s), 8.95(1H, br).

EXAMPLE 48

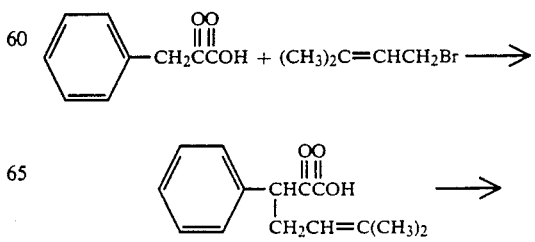

-continued

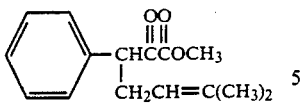

A 1N aqueous solution of sodium hydroxide (20 ml: 20 mmoles) was added to 1.64 g (10 mmoles) of phenylpyruvic acid to form a solution. Then 1.49 g (10 mmoles) of prenyl bromide was added, and the mixture was reacted at room temperature for 13 hours. The reaction mixture was acidified with 1N hydrochloric acid, and extracted with three 50 ml portions of the ether. The organic layers were dried over magnesium sulfate, and the ether was evaporated under reduced pressure to give 2-oxo-3-phenyl-6-methyl-5-heptenoic acid as a pale yellowish white solid. The product was converted to a methyl ester using diazomethane, and the methyl ester was purified by silica gel column chromatography to give methyl 2-oxo-3-phenyl-6-methyl-5-heptenoate as a nearly pure product (1.72 g; yield 70 %).

$^1$H-NMR spectrum (CDCl$_3$, ppm): 1.50(3H, br s), 1.58(3H, br s), 2.41(1H, m), 2.70(1H, m), 4.45(1H, t, J=6.9Hz), 4.94(1H, m), 7.21(5H, s), 8.95(1H, br).

IR spectrum (KBr, cm$^{-1}$) 1730, 1270, 1240.

Elemental analysis values (calculated, C$_{15}$H$_{18}$O$_3$, %): C, 73.08(73.15); H, 7.25(7.37).

EXAMPLE 49

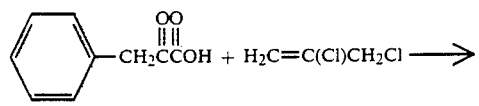

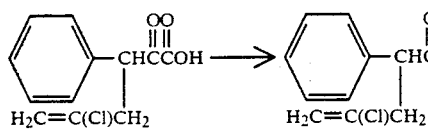

By the same operation as in Example 45, 1.64 g (10 mmoles) of phenylpyruvic acid was reacted with 0.11 g (10 mmoles) of 2,3-dichloropropene in a 1N aqueous solution of sodium hydroxide (20 ml, 20 mmoles) to give 2-oxo-3-phenyl-5-chloro-5-hexenoic acid as a pale yellowish white solid. It was converted to a methyl ester by using diazomethane, and then the methyl ester was purified by silica gel column chromatography. Methyl 2-oxo-3-phenyl-5-chloro-5-hexenoate as a pure product (1.87 g; yield 74 %) was obtained.

$^1$H-NMR spectrum (CDCl$_3$, ppm): δ2.73(1H, dd J=6.9 and 15.0Hz), 3.15(1H, dd, J=6.9 and 15.0Hz), 4.90(1H, t, J=6.9Hz), 5.02(1H, m), 5.08(1H, m), 7.25(5H, s), 8.60(1H, br).

IR spectrum (KBr, cm$^{-1}$) 1730, 1640, 1280, 1240.

Elemental analysis values (calculated, C$_{13}$H$_{13}$ClO$_3$, %): C, 61.89(61.79); H, 5.15(5.19).

EXAMPLE 50

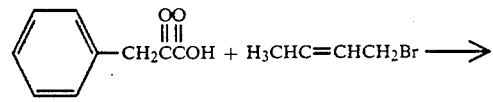

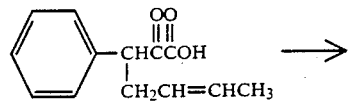

A 1N aqueous solution of sodium hydroxide (6 ml, 6 mmoles) was added to 0.49 g (5.0 mmoles) of phenylpyruvic acid to form a solution. Then, 0.5 ml (3.7 mmoles) of crotyl bromide was added, and the mixture was stirred at room temperature for 13 hours. The reaction mixture was acidified with 1N hydrochloric acid and extracted with three 30 ml portions of ether. The ether layers were dried over magnesium sulfate, and then the ether was evaporated under reduced pressure to obtain a pale brown oil. The NMR spectral analysis of this product led to the determination that this product was nearly pure 2-oxo-3-phenyl-5-heptenoic acid (0.17 g; yield 99%).

$^1$H-NMR spectrum (CDCl$_3$, TMS, ppm): δ1.65(3H, d, J=4.8Hz), 2.75(2H, m), 4.63(1H, J=7.2Hz), 4.86-5.96(2H, m), 7.31(5H, s).

This product was isolated as a pure sodium salt by using an aqueous solution of sodium hydroxide.

Melting point: more than 300° C.

IR spectrum (KBr, cm$^{-1}$) 1700, 1640, 1400.

Elemental analysis values (calculated, C$_{13}$H$_{13}$O$_3$-Na•2/3H$_2$O, %): C, 58.84(58.42); H, 5.03(6.03).

EXAMPLE 51

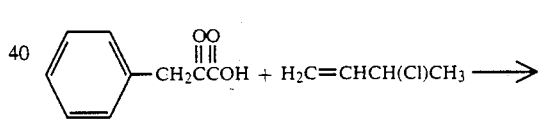

By the same way as in Example 45, 1.64 g (10 mmoles) of phenylpyruvic acid reacted at room temperature for 13 hours with 3-chloro-1-butene (0.91 g; 10 mmoles) in an aqueous solution of 1N sodium hydroxide (20 ml, 20 mmoles). As a result, 2-oxo-3-phenyl-5-heptenoic acid and 2-oxo-3-phenyl-4-methyl-5-hexenoic acid reacted at the 1-position and 3-position of 3-chloro-1-heptene were obtained. A mixture of these compounds was converted into a methyl ester using diazomethane. The NMR spectrum of this product showed that the ratio of the ester products obtained was 1:1, and the total amount was 77 %.

$^1$H-NMR spectrum (ester mixture) (CDCl$_3$, ppm): δ0.80 and 1.33 (total 3H, each d, J=4.8Hz), 1.57(3H, d, J=3.2Hz), 2.1-2.8(3H, m), 3.71(6H, s), 4.43(2H, t, J=4.8Hz), 4.8-5.2(2H, m), 5.25-5.95(4H, m), 7.27(10H, m).

EXAMPLE 52

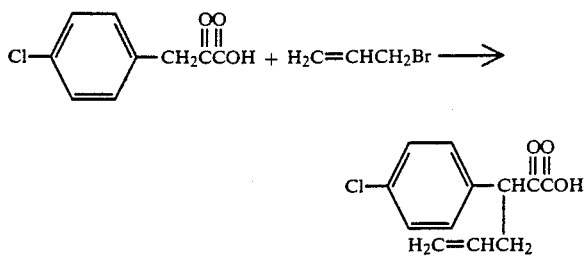

A 1N aqueous solution of sodium hydroxide (10 ml; 10 mmoles) was added to 1.0 g (5.0 mmoles) of P-chlorophenylpyruvic acid to form a solution. Then, 0.91 g (7.5 mmoles) was added, and the mixture was stirred at room temperature for 13 hours. The reaction mixture was acidified with 1N hydrochloric acid, and extracted with three 10 ml portions of ethyl acetate. The organic layers were dried over magnesium sulfate, and the ether was evaporated under reduced pressure to give a pale yellow product. The NMR spectral analysis of this product led to the determination that 2-oxo-3-(p-chlorophenyl)-5-hexenoic acid formed in a yield of 73 %.

$^1$H-NMR spectrum (CDCl$_3$, ppm): δ2.49(1H, m), 2.78(1H, m), 4.50(1H, t, J=6.9Hz), 4.93(1H, m), 4.97(1H, m), 5.99(1H, m), 7.23(4H, s), 9.37(1H, br).

EXAMPLE 53

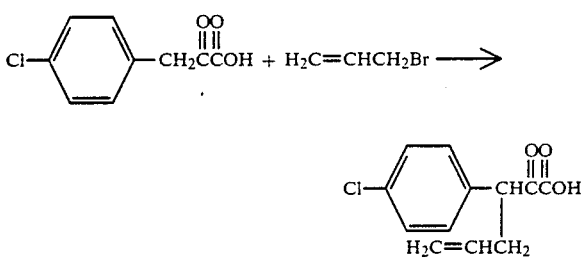

By the same operation as in Example 45 except that 10 ml of 1N sodium hydroxide was used as the base, 2-oxo-3-(p-chlorophenyl)-5-hexenoic acid was obtained in a yield of 80 % from 1.0 g (5.0 mmoles) of p-chlorophenylpyruvic acid and 0.91 g (7.5 mmoles) of allyl bromide.

EXAMPLE 54

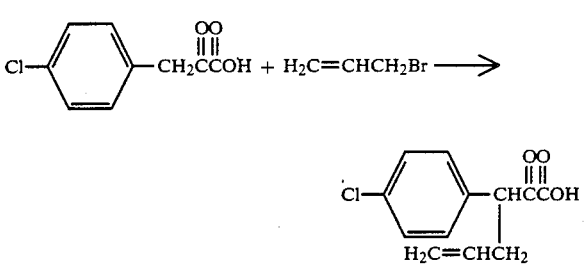

By the same operation as in Example 45 except that 10 ml of 1N potassium hydroxide was used as the base, 2-oxo-3-(p-chlorophenyl)-5-hexenoic acid was obtained in a yield of 61 % from 1.0 g (5.0 mmoles) of p-chlorophenylpyruvic acid and 0.91 g (7.5 mmoles) of allyl bromide.

EXAMPLE 55

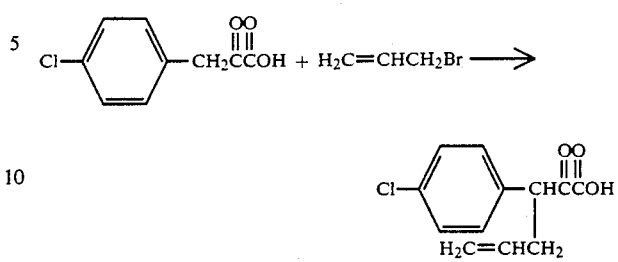

By the same operation as in Example 45 except that 10 ml of an aqueous solution of 0.19 g (2.5 mmoles) of potassium hydroxide was used as the base, 2-oxo-3-(p-chlorophenyl)-5-hexenoic acid was obtained in a yield of 65 % from 1.0 g (5.0 mmoles) of p-chlorophenylpyruvic acid and 1.21 g (10 mmoles) of allyl bromide.

EXAMPLE 56

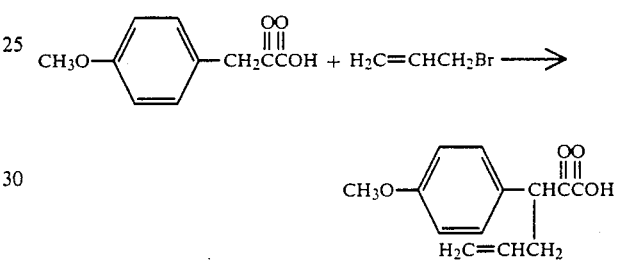

By the same operation as in Example 45 except that p-methoxyphenylpyruvic acid was used as the aromatic pyruvic acid, 2-oxo-3-(p-methoxyphenyl)-5-hexenoic acid was obtained nearly quantitatively from 1.0 g (5.1 mmoles) of p-methoxyphenylpyruvic acid and 5.1 mmoles of allyl bromide using a 1N aqueous solution of sodium hydroxide (1.0 g; 5.1 mmoles) as the base.

$^1$H-NMR spectrum (CDCl$_3$, TMS, ppm): δ2.48(1H, m), 2.75(1H, m), 3.76(3H, s), 4.53(1H, t, J=7.2Hz), 4.94(1H, m), 5.00(1H, m), 5.68(1H, ddt, J=17.7, 10.5, and 6.0Hz), 6.83(2H, d, J=8.4Hz), 7.18(1H, d, J=8.4Hz), 9.95(1H, br).

EXAMPLE 57

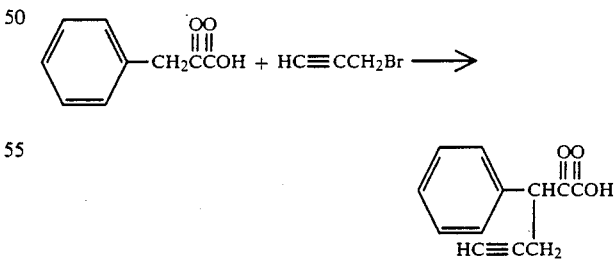

A 1N aqueous solution of sodium hydroxide (20 ml; 20 mmoles) was added to 1.64 g (10 mmoles) of phenylpyruvic acid to form a solution. Then, 1.19 g (10 mmoles) of propargyl bromide was added, and the mixture was stirred at room temperature for 13 hours. The reaction mixture was acidified with 1N hydrochloric acid and extracted with three 50 ml portions of ether. The ether layers were dried over magnesium sulfate, and the ether was evaporated under reduced pressure to give a pale yellowish white solid. The NMR spectral analysis of this product led to the determination that nearly pure 2-oxo-3-phenyl-5-hexynoic acid (1.88 g; yield 93 %).

$^1$H-NMR spectrum (CDCl$_3$, ppm): δ1.90(1H, t, J=2.4Hz), 2.59(1H, ddd, J=2.4, 6.9, and 18.0Hz), 2.92(1H, ddd, J=2.4, 6.9, and 18.0Hz), 4.72(1H, t, J=6.9Hz), 7.25(5H, s), 8.88(1H, br).

IR spectrum (KBr, cm$^{-1}$) 2105, 1735, 1710, 1280.

Elemental analysis values (calculated, C$_{12}$H$_{10}$O$_3$, %): C, 71.09(71.28); H, 5.01(4.98).

EXAMPLE 58

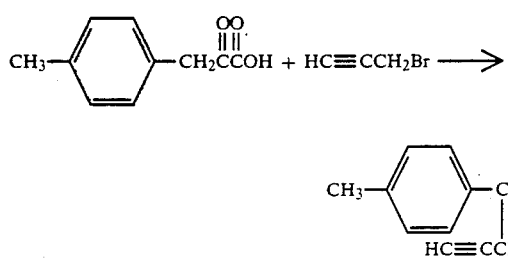

A 2N aqueous solution of sodium hydroxide (10 ml; 20 mmoles) was added to 1.78 g (10 mmoles) of p-methylphenylpyruvic acid to form a solution. Then, 0.9 ml (12 mmoles) of propargyl bromide was added, and the mixture was stirred at room temperature for 8 hours. The reaction mixture was acidified with 1N hydrochloric acid and extracted with three 50 ml portions of ether. The ether layers were dried over magnesium sulfate, and concentrated under reduced pressure to give a pale yellowish white product. The NMR spectral analysis of this product led to the determination that 2-oxo-3-(p-methylphenyl)-5-hexynoic acid formed in a yield of 50 %. This product was purified by silica gel column chromatography to give a pure product.

Melting point: 104°–110° C.

$^1$H-NMR spectrum (CDCl$_3$-DMSO-d$_6$, ppm): δ2.05(1H, t, J=2.2Hz), 2.26(3H, s), 2.53(1H, ddd, J=2.4, 12.8, and 14.4Hz), 2.77(1H, ddd, J=2.4, 12.8, and 14.4Hz), 4.54(1H, t, J=7.2Hz), 7.04(4H, s).

IR spectrum (KBr, cm$^{-1}$) 2100, 1710, 1260.

Elemental analysis values (calculated, C$_{13}$H$_{12}$O$_3$, %): C, 72.16(72.20); H, 5.84(5.59).

EXAMPLE 59

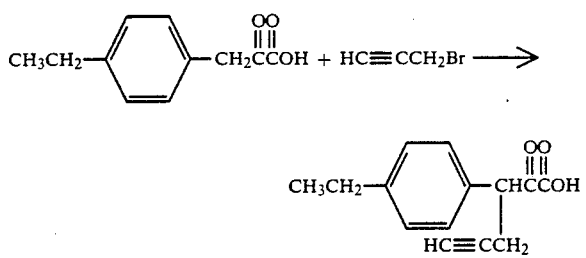

A 2N aqueous solution of sodium hydroxide (3 ml; 6 mmoles) was added to 0.6 g (3 mmoles) of 2-ethylphenylpyruvic acid to form a solution. Then, 0.3 ml (4 mmoles) of propargyl bromide was added, and the mixture was stirred at room temperature for 12 hours. The reaction mixture was acidified with 1N hydrochloric acid and extracted with three 30 ml portions of ether.

The ether layers were dried over magnesium sulfate and concentrated under reduced pressure to give a pale yellowish white product. The NMR spectral analysis of this product led to the determination that 2-oxo-3-(p-ethylphenyl)-5hexynoic acid formed in a yield of 72 %.

$^1$H-NMR spectrum (CDCl$_3$-DMSO-d$_6$, ppm) δ1.20(3H, t, J=7.0Hz), 1.91(1H, t, J=2.2Hz), 2.27(2H, q, J=7.0Hz), 2.63(1H, ddd, J=2.8, 12.2, and 14.0Hz), 2.89(1H, ddd, J=2.2, 12.2, and 14.0Hz), 4.69(1H, t, J=7.2Hz), 7.12(4H, s), 8.64(1H, br s).

EXAMPLE 60

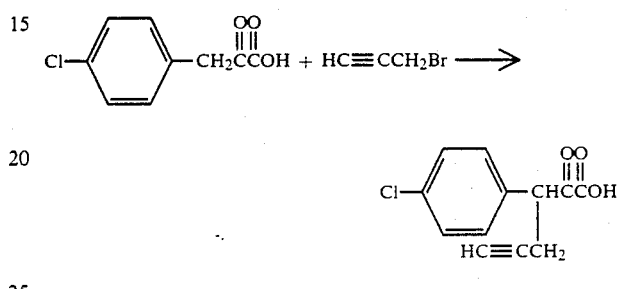

A 2N aqueous solution of sodium hydroxide (20 ml, 40 mmoles) was added to 3.97 g (20 mmoles) of p-chlorophenylpyruvic acid to form a solution. Then, 1.8 ml (24 mmoles) of propargyl bromide was added, and the mixture was stirred at room temperature for 12 hours. The reaction mixture was acidified with 1N hydrochloric acid, and extracted with three 50 ml portions of ether. The ether layers were dried over magnesium sulfate, and concentrated under reduced pressure to give a pale yellowish white product. The NMR spectral analysis of this product led to the determination that 2-oxo-3-(p-chlorophenyl)-5-hexynoic acid formed in a yield of 98 %.

Melting point: 108°–115° C.

$^1$H-NMR spectrum (CDCl$_3$-DNSO-d$_6$, ppm) δ2 40(1H, t, J=2.2Hz), 2.73(2H, m), 4.56(1H, t, J=6.8Hz), 7.25(4H, s).

IR spectrum (KBr, cm$^{-1}$) 2100, 1720, 1260.

Elemental analysis values (calculated, C$_{12}$H$_9$ClO$_3$, %): C, 60.75(60.90); H, 4.09(3.83).

EXAMPLE 61

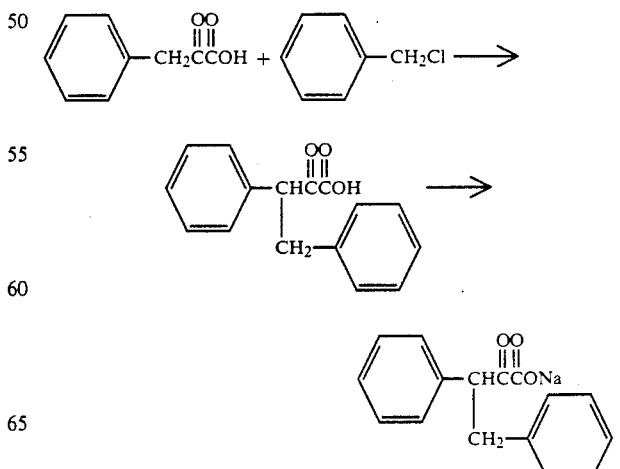

A 3N aqueous solution (10 ml) of sodium hydroxide, 20 ml of methanol, 0.8 g of potassium iodide and 100 mg of triethylbenzylammonium chloride were added to 1.64 g (10.0 mmoles) of phenylpyruvic acid to form a solution. Then, 1.6 ml of benzyl chloride was added, and the mixture was stirred at room temperature for 24 hours. The reaction mixture was acidified with 1N hydrochloric acid and extracted with 100 ml of ether. The ether layer was dried over magnesium sulfate and concentrated under reduced pressure to give a white solid. The NMR spectrum of the product led to the determination that 2-oxo-3,4-diphenylbutanoic acid formed in a yield of 89 %.

¹H-NMR spectrum (CDCl₃-DNSO-d₆, TMS, ppm): δ2.93(1H, dd, J=7.2 and 7.6Hz), 3.40(1H, dd, J=7.2 and 7.6Hz), 4.73(1H, t, J=7.8Hz), 7,10(5H, s), 7.20(5H, s).

This product was isolated as a pure sodium salt by using an aqueous solution of sodium hydroxide.

Melting point: 165°–170° C.

IR spectrum (KBr, cm⁻¹) 1710, 1635, 1390.

Elemental analysis values (calculated, C₁₆H₁₃O₃·Na•1/3H₂O, %) C, 68.03(68.08); H, 4.57(4.88).

EXAMPLE 62

By the same operation as in Example 61 except that 6 ml of tetrahydrofuran was used as the solvent, 2-oxo-3,4-diphenylbutanoic acid formed in a yield of 68 % by the reaction of 0.49 g (3 mmoles) of phenylpyruvic acid with 0.5 ml of benzyl chloride, as determined by NMR spectral analysis.

EXAMPLE 63

By the same operation as in Example 61 except that 6 ml of 1,4-dioxane was used as the solvent, 2-oxo-3,4-diphenylbutanoic acid formed in a yield of 63 % by the reaction of 0.49 g (3 mmoles) of phenylpyruvic acid with 0.5 ml of benzyl chloride, as determined by NMR spectral analysis.

EXAMPLE 64

By the same operation as in Example 61 except that 6 ml of acetonitrile was used as the solvent, 2-oxo-3,4-diphenylbutanoic acid formed in a yield of 66 % by the reaction of 0.49 g (3 mmoles) of phenylpyruvic acid with 0.5 ml of benzyl chloride, as determined by NMR spectral analysis.

EXAMPLE 65

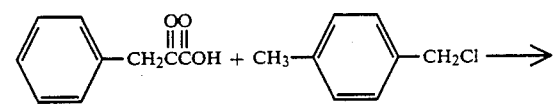

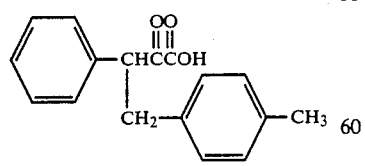

A 3N aqueous solution (4 ml) of sodium hydroxide, 10 ml of tetrahydrofuran, 50 mg of potassium iodide and 100 mg of triethylbenzylammonium chloride were added to 0.82 g (5.0 mmoles) of phenylpyruvic acid to form a solution. Then, 0.8 ml of p-methylbenzyl chloride was added, and the mixture was stirred at room temperature for 36 hours. The reaction mixture was acidified with 1N hydrochloric acid, and extracted with 100 ml of ether. The ether layer was dried over magnesium sulfate and concentrated under reduced pressure to give a pale yellowish white solid. The NMR spectral analysis of this product led to the determination that 2-oxo-3-phenyl-4-(p-methylphenyl)butanoic acid formed in a yield of 24 %.

¹H-NMR spectrum (CDCl₃, TMS, ppm): δ2.23(3H, s), 3.11(2H, m), 4.78(1H, t, J=7.0Hz), 6.94(5H, s), 7.20(5H, s), 9.26(1H, br s).

EXAMPLE 66

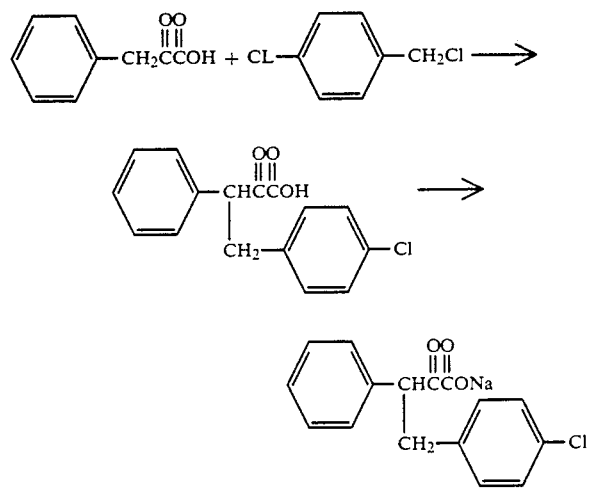

A 3N aqueous solution (4 ml) of sodium hydroxide, 10 ml of tetrahydrofuran, 100 mg of potassium iodide and 100 mg of triethylbenzylammonium chloride were added to 0.83 g (5.0 mmoles) of phenylpyruvic acid to form a solution. Then, 0.8 ml of p-chlorobenzyl chloride was added, and the mixture was stirred at room temperature for 36 hours. The reaction mixture was acidified with 1N hydrochloric acid and extracted with 100 ml of ether. The ether layer was dried over magnesium sulfate and concentrated under reduced pressure to give a pale yellowish white oil. A 1N aqueous solution of sodium hydroxide was added to the product, and the mixture was concentrated under reduced pressure. Ether was added to the resulting semi-soid mixture, and the precipitated sodium 2-oxo-3-phenyl-4-(p-chlorophenyl)butanoate was isolated by filtration as a white solid (yield 37 %).

Melting point: 200°–206° C.

¹H-NMR spectrum (DMS TMS, ppm): δ2.26-3.76(2H, m), 4.91(1H, t, J=7.8Hz), 7.00(5H, s), 7.23(5H, s).

IR spectrum (KBr, cm ): 1700, 1630, 1390.

EXAMPLE 67

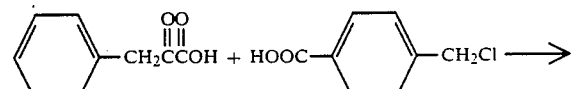

-continued

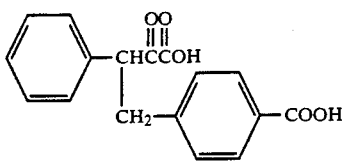

A 3N aqueous solution (3 ml) of sodium hydroxide, 6 ml of tetrahydrofuran, 30 mg of potassium iodide and 30 mg of triethylbenzylammonium chloride were added to 0.49 g (3.0 mmoles) of phenylpyruvic acid to form a solution. Then, a solution of 1.4 ml of p-carboxybenzyl chloride in 6 ml of methanol was added, and the mixture was stirred at room temperature for 18 hours. The reaction mixture was acidified with 1N hydrochloric acid and extracted with 100 ml of ether. The ether layer was dried over magnesium sulfate and concentrated under reduced pressure to give a pale yellowish white solid. The NMR spectral analysis of this product led to the determination that 2-oxo-3-phenyl-4-(p-carboxyphenyl)butanoic acid formed in a yield of 73 %.

$^1$H-NMR spectrum (CDCl$_3$-DMSO-d$_6$, ppm): δ3.19(2H, m), 4.71(1H, t, J=7.4Hz), 7.43(2H, d, J=7.8Hz), 7.46(5H, s), 7.92(2H, d, J=7.8Hz).

EXAMPLE 68

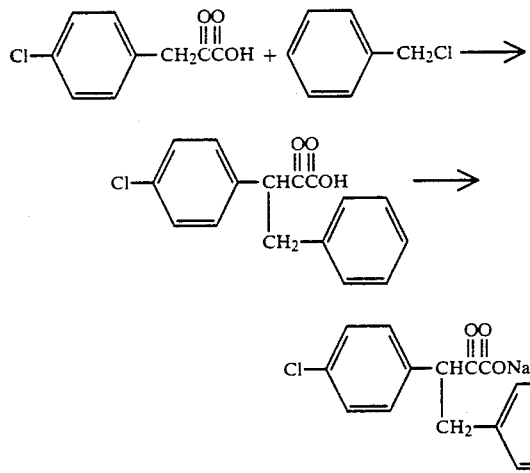

A 3N aqueous solution (8 ml) of sodium hydroxide, 20 ml of tetrahydrofuran, 100 mg of potassium iodide and 100 mg of triethylbenzylammonium chloride were added to 1.98 g (10 mmoles) of p-chlorophenylpyruvic acid to form a solution. Then, 1.4 ml of benzyl chloride was added, and the mixture was stirred at room temperature for 18 hours. The reaction mixture was acidified with 1N hydrochloric acid, and extracted with 100 ml of ether. The ether layer was dried over magnesium sulfate and concentrated under reduced pressure to give a pale yellowish white solid. The NMR spectral analysis of this product led to the determination tat 2-oxo-3-(p-chlorophenyl)-4-phenylbutanoic acid formed in a yield of 74 %.

$^1$H-NMR spectrum (CDCl$_3$-DNSO-d$_6$, ppm): δ3.15(2H, m), 4.73(1H, t, J=7.2Hz), 7.08 (4H, s), 7.16(5H, s).

Then, 3.7 ml of a 2N aqueous solution of sodium hydroxide was added to the resulting product, and the mixture was concentrated under reduced pressure. Ether was added, and the precipitated white solid was isolated by filtration to give sodium 2-oxo-3-(p-chlorophenyl)-4-phenylbutanoate in a yield of 45 %.

Melting point: 205°-210° C.

$^1$H-NMR spectrum (CDCl$_3$-DNSO-d$_6$, ppm): δ2.65-3.59(2H, m), 4.87(1H, t, J=7.2Hz), 7.09(4H, s), 7.18(5H, s).

IR spectrum (KBr, cm$^{-1}$) 1710, 1660, 1385.

Elemental analysis values (calculated, C$_{16}$H$_{12}$ClO$_3$Na•3/2H$_2$O, %): C, 56.85(56.90); H, 3.52(4.48).

EXAMPLE 69

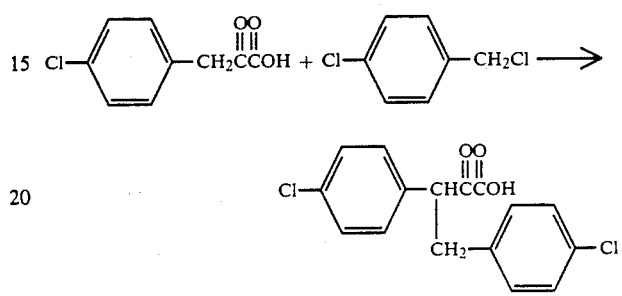

A 3N aqueous solution (3 ml) of sodium hydroxide, 8 ml of tetrahydrofuran, 40 mg of potassium iodide and 40 mg of triethylbenzylammonium chloride were added to 0.79 g (4.0 mmoles) of p-chlorophenylpyruvic acid to form a solution. Then, 1.4 ml of p-chlorobenzyl chloride was added, and the mixture was stirred at room temperature for 12 hours. The reaction mixture was acidified with 1N hydrochloric acid and extracted with ether. The ether layer was dried over magnesium sulfate and concentrated under reduced pressure to give a pale yellowish white solid. The NMR spectral analysis of this product led to the determination that 2-oxo-3-(p-chlorophenyl)-4-(p-chlorophenyl)butanoic acid formed in a yield of 72 %.

$^1$H-NMR spectrum (CDCl$_3$, TMS, ppm): δ3.17(2H, m), 4.69(1H, t, J=7.4Hz), 7.03(4H, s), 7.19(4H, s).

EXAMPLE 70

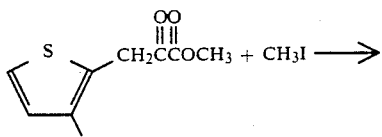

A 3N aqueous solution of sodium hydroxide (6.0 mmoles) was added to a solution of 0.5 g (2.5 mmoles) of 3-methyl-2-thienylpyruvate in 6 ml of methanol. The mixture was stirred at room temperature until it became uniform. Then, 0.27 ml (7.6 mmoles) of methyl iodide was added, and the mixture was stirred at room temperature for 19 hours. The reaction mixture was acidified with 1N hydrochloric acid and extracted with three 60 ml portions of ether. The ether layers were dried over magnesium sulfate and concentrated under reduced pressure to give a yellowish brown oil. The product was purified by silica gel column chromatography (hexane:ethyl acetate=5:1) to give 185 mg (0.93 mmoles) of 2-oxo-3-methyl-3-(3-methyl-thienyl)butanoic acid in a yield of 37 %.

$^1$H-NMR spectrum (CDCl$_3$-DMSO-d$_6$, TMS, ppm): δ1.50(3H, d), 2.23(3H, s), 4.87(2H, q), 6.80(1H, d, J=4.8Hz), 7.14(1H, d, J=4.8Hz), 8.90-9.30(1H, br s).

EXAMPLE 71

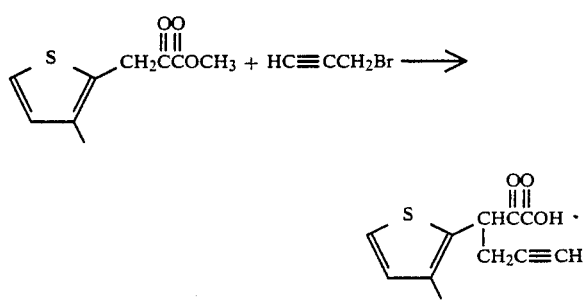

A methanol solution (6.0 mmoles) of sodium hydroxide prepared in advance was added to 0.5 g (2.5 mmoles) of 3-methyl 3-methyl-2-thienylpyruvate, and the mixture was stirred at room temperature until it became uniform. Then, an excess of propargyl bromide was added, and the mixture was stirred for 12 hours. The reaction mixture was acidified with 1N hydrochloric acid, and extracted with 50 ml of ether. The ether layer was dried over magnesium sulfate and concentrated under reduced pressure to give a simple yellow oil. It was purified by silica gel column chromatography to give 0.28 g (1.18 mmoles) of 2-oxo-3-(3-methyl-2-thienyl)-4-hexynoic acid in a yield of 47 %.

$^1$H-NMR spectrum (CDCl$_3$, TMS, ppm): δ1.93(1H, t, J=2.5Hz), 2,27(3H, s), 2.65(1H, ddd, J=18.0, 7.5, and 2.5Hz), 2.95(1H, ddd, J=18.0, 7.5, and 2.5Hz), 5.08(1H, t, J=7.5Hz), 6.80(1H, d, J=5.0Hz), 7.18(1H, d, J=5.0Hz), 8.45(1H, br s).

IR spectrum (KBr, cm$^{-1}$) 2140, 1720, 1240.

EXAMPLE 72

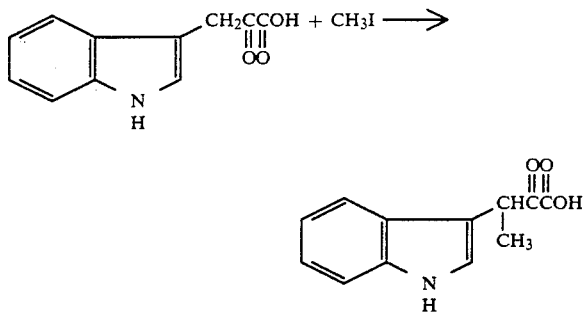

A 3N aqueous solution of sodium hydroxide (1.86 mmoles) was added to a solution of 0.2 g (0.93 mmole) of 3-indolylpyruvic acid in 5 ml of methanol, and the mixture was stirred at room temperature until it became uniform. Then, 0.1 ml (2.8 mmoles) of methyl iodide was added, and the mixture was stirred at room temperature for 4 hours. The reaction mixture was acidified with 1.9 ml of 1N hydrochloric acid, and extracted with three 20 ml portions of ether. The ether layers were dried over magnesium sulfate and concentrated under reduced pressure to give a yellow oil. The NMR spectral analysis of this product led to the determination that 2-oxo-3-methyl-3indolylbutanoic acid formed in a yield of 67 %.

$^1$H-NMR spectrum (CDCl$_3$-DMSO-d$_6$, TMS, ppm): δ1.48(3H, d), 4.74(1H, q), 7.00-7.38(3H, m), 7.46-7.64(1H, m), 7.72-8.00(1H, m), 9.10-10.0(2H, m).

EXAMPLE 73

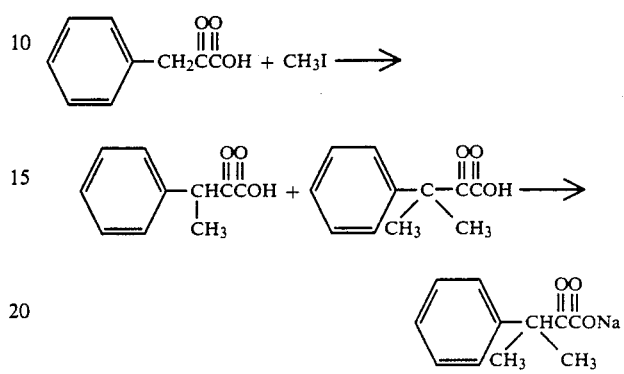

A 2N aqueous solution (58.5 ml) of sodium hydroxide and 100 ml of tetrahydrofuran were added to 6.35 g (39 mmoles) of phenylpyruvic acid, and the mixture was stirred until a completely uniform solution formed. Then, 6.4 ml (98 mmoles) of methyl iodide was added, and the mixture was reacted at a room temperature for 12 hours. The reaction mixture was acidified with 1N hydrochloric acid, and extracted with ether. The ether layer was dried over magnesium sulfate. The drying reagent was removed by filtration, and the solvent was evaporated. The NMR spectral analysis of the resulting oil led to the determination that 2-oxo-3-methyl-3-phenylbutanoic acid and 2-oxo-3-phenylbutanoic acid formed in a yield of 59 % and 12 %, respectively.

The NMR spectrum of 2-oxo-3-methyl-3-phenylbutanoic acid is shown below. The NMR spectrum of 2-oxo-3-phenylbutanoic acid is as shown in Example 1.

$^1$H-NMR spectrum (CDCl$_3$, ppm): δ1.60(6H, s), 7.20(5H, s).

Then, 10.7 ml of a 2N aqueous solution of sodium hydroxide was added to the above product, and the mixture was concentrated under reduced pressure. Ether was added, and the precipitated white solid was isolated by filtration to give nearly pure sodium 2-oxo-3-methyl-3-phenylbutanoate (3.4 g; 15.8 mmoles) in a yield of 41 %.

Melting point: 232°-238° C.

$^1$H-NMR spectrum (CDCl$_3$-DMSO-d$_6$, ppm): δ1.53(6H, s), 7.23(5H, m). 1R spectrum (KBr, cm$^{-1}$) 1720, 1680.

Elemental analysis values (calculated, C$_{11}$H$_{11}$O$_3$·Na·H$_2$O, %): C, 57.16(56.92); H, 4.55(5.65).

EXAMPLE 74

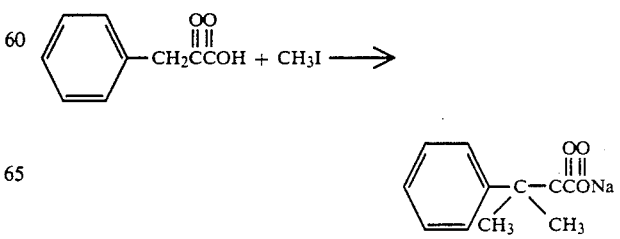

A 2N aqueous solution (15 ml of sodium hydroxide and 20 ml of tetrahydrofuran were added to 1.64 g (10 mmoles) of phenylpyruvic acid, and the mixture was stirred until a completely uniform solution formed. Then, 1.5 ml (24 mmoles) of methyl iodide was added, and the mixture reacted at room temperature for 12 hours. After the reaction, the solvent was removed under reduced pressure. A mixed solvent of ethanol and ether was added to the resulting semi-solid product, and the precipitated sodium 2-oxo-3-methyl-phenylbutanoate (1.92 g; yield was isolated by filtration.

EXAMPLE 75

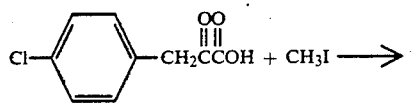

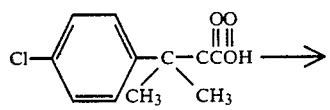

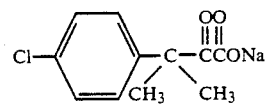

A 3N aqueous solution (13.8 ml) of sodium hydroxide and 30 ml of tetrahydrofuran were added to 2.73 g (13.8 mmoles) of p-chlorophenylpyruvic acid, and the mixture was stirred until a completely uniform solution formed. Then, 2.5 ml (34.5 mmoles) of methyl iodide was added, and the mixture reacted at room temperature for 18 hours. The reaction mixture was acidified with 1N hydrochloric acid, and extracted with ether. The ether layer was dried over magnesium sulfate. The drying reagent was separated by filtration and the solvent was evaporated. The NMR spectral analysis of the resulting oil led to the determination that 2-oxo-3-methyl-3-(p-chlorophenyl)butanoic acid formed. Then, a 1N aqueous solution (13 ml) of sodium hydroxide was added, and the mixture was concentrated under reduced pressure. Ether was added, and the precipitated white solid was isolated by filtration to give 1.48 g (5.37 mmoles) of sodium 2-oxo-3-methyl-3-(p-chlorophenyl)-butanoate in a yield of 43%.

Melting point: 260°–267° C.
$^1$H-NMR spectrum (CDCl$_3$-DMSO-d$_6$, ppm): δ1.53(6H, s), 7.25(4H, s).
IR spectrum (KBr, cm$^{-1}$) 1710, 1655.
Elemental analysis values (calculated, C$_{11}$H$_{10}$ClO$_3$-Na·½H$_2$O, %): C, 51.59(51.28); H, 3.89(4.30).

EXAMPLE 76

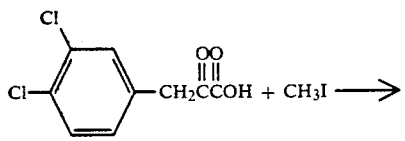

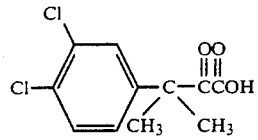

A 2.4N aqueous solution (250 ml) of sodium hydroxide and 100 ml of tetrahydrofuran were added to 23.3 g (100 mmoles) of 3,4-dichlorophenylpyruvic acid, and the mixture was stirred until a completely uniform solution formed. Then, 85 g (599 mmoles) of methyl iodide and 0.2 g of tetrabutyl ammonium bromide were added, and the mixture reacted at room temperature for 48 hours. The reaction mixture was acidified with 1N hydrochloric acid and extracted with two 200 ml portions of ether. The ether layers were washed with a 5 % aqueous solution of sodium thiosulfate, washed with water, and dried over magnesium sulfate. The drying reagent was separated by filtration, and the solvent was evaporated. The NMR spectral analysis of the product led to the determination that the white solid formed was 2-oxo-3-methyl-3-(3,4-dichlorophenyl)butanoic acid (25.0 g; yield 96 %).

Melting point: 83°–86° C. $^1$H-NMR spectrum (CDCl$_3$, TMS, ppm): δ1.63(6H, s), 6.97-7.45(3H, m), 10.25(1H, bs).

EXAMPLE 77

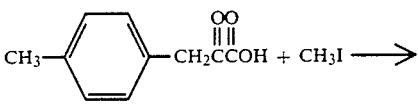

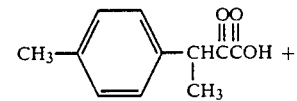

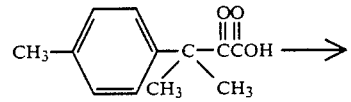

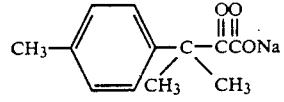

A 3N aqueous solution (4 ml) of sodium hydroxide and 15 ml of tetrahydrofuran were added to 0.53 g (3.0 mmoles) of p-methylphenylpyruvic acid, and the mixture was stirred until a completely uniform solution formed. Then, 1.0 ml (15 mmoles) of methyl iodide was added, the mixture reacted at room temperature for 4.5 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil led to the determination that 2-oxo-3-methyl-3-(p-methylphenyl)butanoic acid and 2-oxo-3-(p-methylphenyl)butanoic acid formed in a yield of 47 %, and 47 %, respectively. The NMR spectrum of 2-oxo-3-methyl-3-(p-methylphenyl)butanoic acid is show below. $^1$H-

NMR spectrum (CDCl$_3$, ppm): δ1.60(6H, s), 2.25(3H, s), 7.09(4H, s).

This product was purified by silica gel column chromatography (ethyl acetate:hexane=1:8) to give 2-oxo-methyl-3-(p-methylphenyl)butanoic acid (0.23 g; 37 %) Then, 1.1 ml of a 1N aqueous solution of sodium hydroxide was added to this product, and the mixture was concentrated under reduced pressure. Ether was added, and a white solid that precipitated was isolated by filtration to give sodium 2-oxo-3-methyl-2-(p-methylphenyl)butanoate (0.25 g; 1.07 mmoles) in a yield of 36 %.

Melting point: 235°-242° C.

$^1$H-NMR spectrum (CDCl$_3$-DMSO-d$_6$, ppm): δ1.56(6H, s), 2.67(3H, s), 6.98(2H, d, J=8.0Hz), 7.29(2H, d, J=8.0Hz).

IR spectrum (KBr, cm$^{-1}$) 1700, 1660.

Elemental analysis values (calculated, C$_{12}$H$_{13}$O$_3$·Na•H$_2$O, %): C, 58.61(58.32); H, 6.32(6.12).

EXAMPLE 78

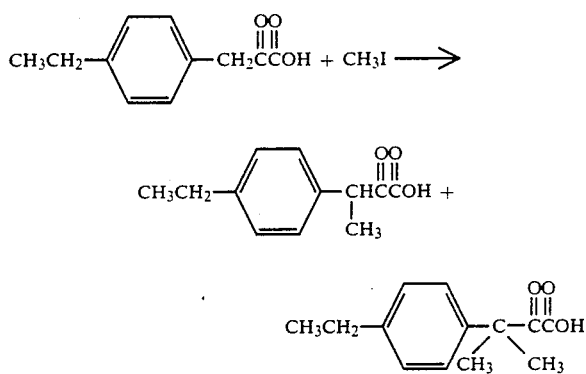

A 3N aqueous solution (2.0 ml) of sodium hydroxide and 10 ml of tetrahydrofuran were added to 0.58 g (3.0 mmoles) of p-methylphenylpyruvic acid, and the mixture was stirred until a completely uniform solution formed. Then, 0.3 ml (4.6 mmoles) of methyl iodide was added, and the mixture reacted at room temperature for 4.5 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oily product led to the determination that the desired 2-oxo-3-methyl-3-(p-methylphenyl)butanoic acid and 2-oxo-3-(p-methylphenyl)butanoic acid formed in a yield of 40%, and 50 %, respectively. The NMR spectrum of 2-oxo-3-methyl-3-(p-methylphenyl)butanoic acid is shown below.

$^1$H-NMR spectrum (CDCl$_3$, ppm): δ1.27(3H, t, J=7.6Hz), 1.63(6H, s), 2.68(2H, q, J=7.6Hz), 7.47(4H, s), 10.13(1H, s).

EXAMPLE 79

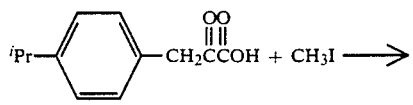

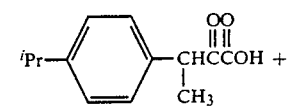

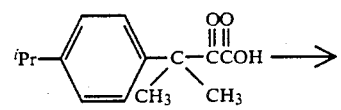

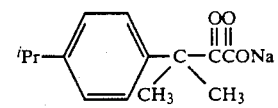

A 3N aqueous solution (10 ml) of sodium hydroxide and 20 ml of tetrahydrofuran were added to 1.03 g (5.0 mmoles) of p-isopropylphenylpyruvic acid, and the mixture was stirred until a completely uniform solution formed. Then, 1.0 g (15 mmoles) of methyl iodide was added, and the mixture reacted at room temperature for 11 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil led to the determination that 2-oxo-3-methyl-3-(p-isopropylphenyl)butanoic acid and 2-oxo-3-(p-isopropylphenyl)butanoic acid formed in a yield of 60 %, and 22 %, respectively. The NMR spectrum of the 2-oxo-3-methyl-(p-isopropylphenyl)butanoic acid is shown below.

$^1$H-NMR spectrum (CDCl$_3$, ppm): δ1.23(6H, d, J=7.0Hz), 1.68(6H, s), 2.95(1H, m), 7.58(4H, s), 8.40(1H, br s).

This product was isolated and purified by silica gel column chromatography (ethyl acetate:hexane=7) to give 2-oxo-3-methyl-3-(p-isopropylphenyl)butanoic acid (0.61 g; yield 52 %). Then, a 1N aqueous solution (1.3 ml) of sodium hydroxide was added to this product, and the mixture was concentrated under reduced pressure. Ether was added and a white solid that precipitated was isolated by filtration to give 0.53 g (2.08 mmoles) of sodium 2-oxo-3-methyl-3-(p-isopropylphenyl)butanoate in a yield of 42 %.

Melting point: 246°-250° C.

$^1$H-NMR spectrum (CDCl$_3$-DMSO-d$_6$, ppm): δ1.17(6H, d, J=7.0Hz), 1.51(6H, s), 2.76(1H, m), 6.96(2H, d, J=9.0Hz), 7.17(2H, d, J=8.0Hz).

IR spectrum (KBr, cm$^{-1}$) 1685, 1640.

Elemental analysis values (calculated, C$_{14}$H$_{17}$O$_3$·Na•5/3H$_2$O, %): C, 58.76(58.73); H, 6.06(7.16).

EXAMPLE 80

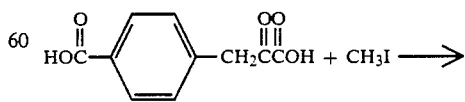

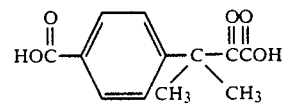

A 3N aqueous solution (70 ml) of sodium hydroxide and 100 ml of tetrahydrofuran were added to 10.0 g (48 mmoles) of p-carboxyphenylpyruvic acid, and the mixture was stirred until a completely uniform solution formed. Then, 6.2 ml (100 mmoles) of methyl iodide was added, and the mixture reacted at room temperature for 24 hours. The reaction mixture was acidified with 1N hydrochloric acid, and extracted with ethyl acetate. The organic layer was dried over magnesium sulfate. The drying reagent was separated by filtration, and the solvent was evaporated. The NMR spectral analysis of the resulting white solid led to the determination that the desired 2-oxo-3-methyl-3-(p-carboxyphenyl)butanoic acid formed in a yield of 90 %. This product was converted to a diester by using diazomethane, and purified by silica gel column chromatography (ethyl acetate:hexane=1:10). Then, a 1N aqueous solution of sodium hydroxide was added to this product to hydrolyze the ester. The product was acidified with 1N hydrochloric acid, and extracted with ether. After drying, the solvent was evaporated to give 7.68 g (32.5 mmoles) of 2-oxo-3-methyl-3-(p-carboxyphenyl)butanoic acid in a yield of 65 %.

Melting point: 144°–163° C.

$^1$H-NMR spectrum (CDCl$_3$-DMSO-d$_6$, ppm): δ1.62(6H, s), 7.30(2H, d, J=8.0Hz), 8.00(2H, d, J=8.0Hz), 9.10(2H, br s).

IR spectrum (KBr, cm$^{-1}$) 3540, 1703, 1680.

EXAMPLE 81

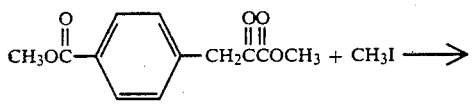

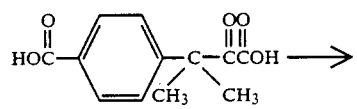

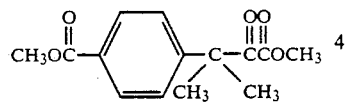

A 1N aqueous solution (50 ml) of sodium hydroxide and 50 ml of tetrahydrofuran were added to 2.33 g (10 mmoles) of methyl p-methoxycarbonylphenylpyruvate, and the mixture was stirred until a completely uniform solution formed. Then, 2.0 ml (32 mmoles) of methyl iodide was added, and the mixture reacted at room temperature for 24 hours. The reaction mixture was acidified with 1N hydrochloric acid and extracted with ethyl acetate. The organic layer was dried over magnesium sulfate, and the solvent was evaporated. The NMR spectral analysis of the resulting white solid led to the determination that 2-oxo-3-methyl-3-(p-carboxyphenyl)butanoic acid formed in a yield of 85 %. This compound was converted to a diester by using diazomethane and then purified by silica gel column chromatography (ethyl acetate:hexane=1:10). By the same operation as in Example 80, 2-oxo-3-methyl-3-(p-carboxyphenyl)butanoic acid (1.32 g; 5.6 mmoles) was obtained in a yield of 56 %.

EXAMPLE 82

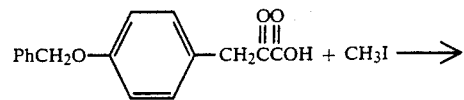

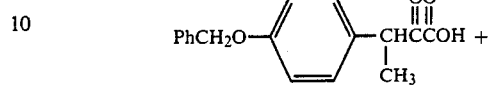

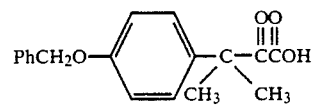

A 3N aqueous solution (6 ml) of sodium hydroxide and 10 ml of tetrahydrofuran were added to 0.49 g (3.0 mmoles) of p-benzyloxyphenylpyruvic acid, and the mixture was stirred until a completely uniform solution formed. Then, 0.5 ml (8 mmoles) of methyl iodide was added, and the mixture reacted at room temperature for 10 hours. The reaction mixture was acidified with 1N hydrochloric acid, and extracted with ether. The ether layer was dried over magnesium sulfate. The drying reagent was separated and the solvent was evaporated. The NMR spectral analysis of the resulting oil led to the determination that 2-oxo-3-methyl-3-(p-benzyloxyphenyl)butanoic acid and 2-oxo-3-(p-benzyloxyphenyl)butanoic acid formed in a yield of 27 % and 33 %, respectively. The NMR spectra of these products are shown below.

2-oxo-3-methyl-3-(p-benzyloxyphenyl)butanoic acid
$^1$H-NMR spectrum (CDCl$_3$, TMS, ppm): δ1.63(6H, s), 5.02(2H, s), 7.38(9H, s), 9.92(1H, br).

2-oxo-3-(p-benzyloxyphenyl)butanoic acid
$^1$H-NMR spectrum (CDCl$_3$, TMS, ppm): δ1.44(3H, d, J=7.2Hz), 5.02(2H, s), 7.38(9H, s), 9.42(1H, br s).

EXAMPLE 83

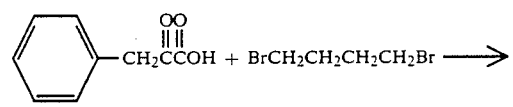

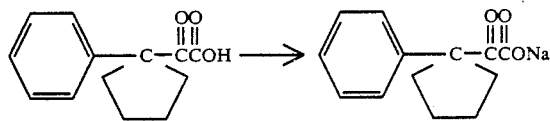

A 3N aqueous solution (5 ml) of sodium hydroxide and 10 ml of tetrahydrofuran were added to 0.82 g (5.0 mmoles) of phenylpyruvic acid, and the mixture was stirred until a completely uniform solution formed. Then, 50 ml of triethyl ammonium chloride, 50 mg of potassium iodide and 0.7 ml (6.04 mmoles) of 1,4-dibromobutane were added, and the mixture reacted at room temperature for 24 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil led to the determination that 1-carboxycarbonyl-1-phenylcyclopentane formed. This product was converted to a methyl ester using diazomethane and purified by silica gel column chromatography (ethyl acetate:hexane=1:20) (0.74 g; yield 58 %). The NMR spectrum of the methyl ester is shown below.

$^1$H-NMR spectrum (CDCl$_3$-DMSO-d$_6$, ppm): δ1.5-2.00(4H, m), 1.83-2.33(2H, m), 2.27-2.67(2H, m), 3.55(3H, s), 7.23(5H, s).

This product was further isolated as its pure sodium salt using sodium hydroxide.

Melting point: 174°-180° C.

IR spectrum (KBr, cm$^{-1}$) 1690, 1630, 1390.

Elemental analysis values (calculated, C$_{13}$H$_{13}$O$_3$·Na•3/4H$_2$O, %): C, 61.06(61.53); H, 5.74(5.76).

EXAMPLE 84

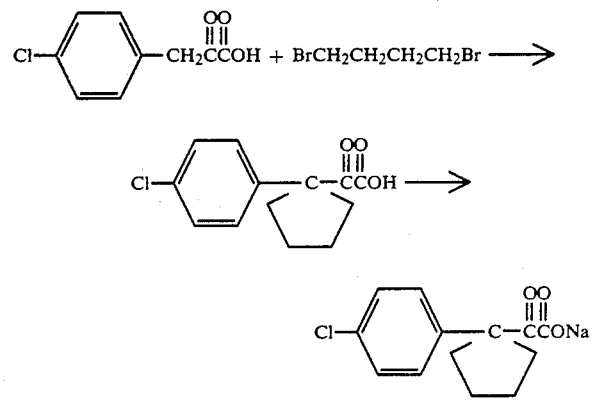

A 3N aqueous solution (5 ml) of sodium hydroxide and 10 ml of tetrahydrofuran were added to 0.99 g (5.0 mmoles) of p-chlorophenylpyruvic acid, and the mixture was stirred until a completely uniform solution formed. Then, 50 mg of triethyl ammonium chloride, 50 mg of potassium iodide and 0.7 ml (6 mmoles) of 1,4-dibromobutane were added, and the mixture reacted at room temperature for 24 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that the desired 1-carboxycarbonyl-1-p-chlorophenylcyclopentane formed in a yield of 58 %.

$^1$H-NMR spectrum (CDCl$_3$, ppm): δ1.50-2.90(6H, m), 2.35-2.80(2H, m), 7.25(4H, s).

Then, 2.0 ml of a 2N aqueous solution of sodium hydroxide was added to this product, and the mixture was concentrated under reduced pressure. Ether was added, and the precipitated white solid was isolated by filtration to give 0.66 g (2.3 mmoles) of sodium salt of 1-carboxycarbonyl-1-p-chlorophenylcyclopentane in a yield of 46%.

Melting point: 237°-242° C.

$^1$H-NMR spectrum (CDCl$_3$-DMSO-d$_6$, ppm): δ1.36-1.66(6H, m), 2.40-2.83(2H, m), 7.18(4H, s).

IR spectrum (KBr, cm$^{-1}$) 1710, 1650, 1400.

EXAMPLE 85

By the same reaction operation as in Example 84 except that 10 ml of a 3N aqueous solution of sodium hydroxide and as the solvent 20 ml of dimethyl sulfoxide were used, 2.39 g (8.2 mmoles) of sodium salt of 1-carboxycarbonyl-1-p-chlorophenylcyclopentane was obtained in a yield of 82 % from 1.98 g (10.0 mmoles) of p-chlorophenylpyruvic acid and 1.4 ml (3.2 mmoles) of 1,4-dibromobutane. EXAMPLE 86

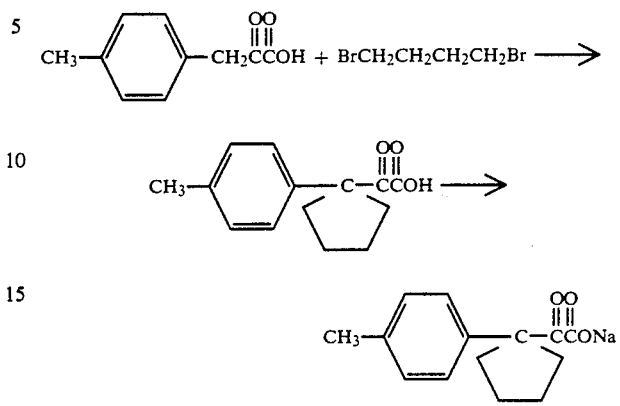

A 3N aqueous solution (5 ml) of sodium hydroxide and 10 ml of tetrahydrofuran were added to 0.89 g (5.0 mmoles) of p-methylphenylpyruvic acid, and the mixture was stirred until a completely uniform solution formed. Then, 50 mg of triethyl ammonium chloride, mg of potassium iodide and 0.7 ml (6 mmoles) of 1,4-dibromobutane were added, and the mixture reacted at room temperature for 48 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil to the determination that 1-carboxycarbonyl-p-methylphenylcyclopentane formed in a yield of 77 %.

$^1$H-NMR spectrum (CDCl$_3$, ppm): δ1.50-2.87(8H, m), 2.27(3H, s), 7.03(4H, s).

A 2N aqueous solution (1.9 ml) of sodium hydroxide was added to this product, and the mixture was concentrated under reduced pressure. Ether was added, and the precipitated white solid was isolated by filtration to give sodium salt of 1-carboxycarbonyl-1-p-methylphenylcyclopentane (0.90 g; 3.5 mmoles) in a yield of 70 %.

Melting point: 208°-212° C.

$^1$H-NMR spectrum (CDCl$_3$-DMSO-d$_6$, ppm): δ1.33-2.00(4H, m), 2.07-2.80(4H, m), 2.25(3H, s), 7.00(2H, d, J=7.5Hz), 7.20(2H, d, J=7.5Hz).

IR spectrum (KBr, cm$^{-1}$) 1700, 1675, 1400.

EXAMPLE 87

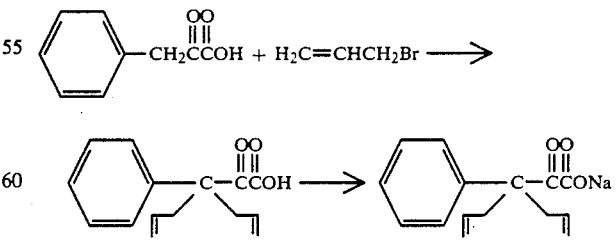

A 2N aqueous solution (10 ml) of sodium hydroxide and 30 ml of tetrahydrofuran were added to 1.64 g (10 mmoles) of phenylpyruvic acid, and the mixture was stirred until a completely uniform solution formed. Then, 100 mg of triethylbenzylammonium chloride and 2.2 ml (25 mmoles) of allyl bromide were added, and the mixture reacted at room temperature for 36 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oil led to the determination that the desired 2-oxo-3-allyl-3-phenyl-5hexenoic acid formed in a yield of 68 %.

Then, 3 ml of a 1N aqueous solution of sodium hydroxide was added to this product, and the mixture was concentrated under reduced pressure. Ether was added, and the precipitated white solid was isolated by filtration to give 1.13 g (4.29 mmole) of sodium 2-oxo-3-allyl-3-phenyl-5-hexenoate in a yield of 43 %.

Melting point: 272°–278° C.

$^1$H-NMR spectrum (CDCl$_3$-DMSO-d$_6$, ppm): δ2.48–3.15(4H, m), 4.27(2H, m), 4.40(2H, m), 7.27(5H, s).

IR spectrum (KBr, cm$^{-1}$) 1710, 1650, 1000, 920.

Elemental analysis values (calculated, C$_{15}$H$_{15}$O$_3$Na, %): C, 67.27(67.66); H, 5.50(5.68).

EXAMPLE 88

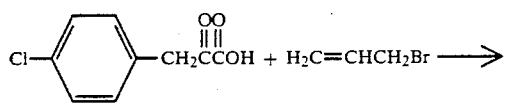

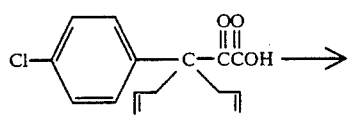

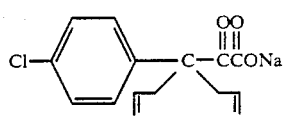

A 3N aqueous solution (10 ml) of sodium hydroxide and 30 ml of tetrahydrofuran were added to 1.98 g (10 mmoles) of p-chlorophenylpyruvic acid, and the mixture was stirred until a completely uniform solution formed. Then, 2.2 ml (25 mmoles) of allyl bromide was added, and the mixture reacted at room temperature for 8 hours. The reaction mixture was acidified with 1N hydrochloric acid, and extracted with ether. The ether layer was dried over magnesium sulfate. The drying reagent was separated by filtration, and the solvent was evaporated. The NMR spectrum of the resulting oil led to the determination that the desired 2-oxo-3-allyl-3-(p-chlorophenyl)-5-hexynoic acid formed in a yield of 62 %.

$^1$H-NMR spectrum (CDCl$_3$, TMS, ppm): δ2.70(4H, m), 4.94(2H, m), 5.09(2H, m), 5.61(2H, m), 7.01(2H, d, J=9.0Hz), 7.57(2H, d, J=9.0Hz), 10.18(1H, br s).

This product was isolated as a pure sodium salt by using sodium hydroxide.

Melting point: 214°–218° C.

IR spectrum (KBr, cm$^{-1}$) 1700, 1640, 1370.

Elemental analysis values (calculated, C$_{15}$H$_{14}$ClO$_3$Na·½H$_2$O, %): C, 58.75(58.17); H, 4.61(4.88).

EXAMPLE 89

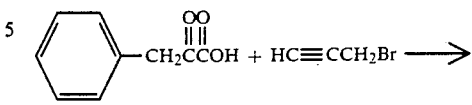

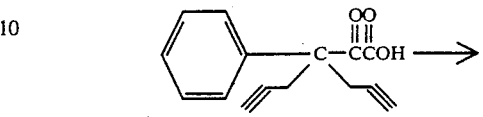

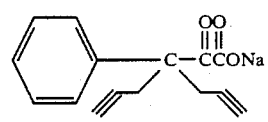

A 3N aqueous solution (5 ml) of sodium hydroxide and 10 ml of tetrahydrofuran were added to 0.82 g (5.0 mmoles) of phenylpyruvic acid, and the mixture was stirred until a completely uniform solution formed. Then, 50 mg of triethylbenzylammonium chloride and 0.9 ml (12 mmoles) of propargyl bromide were added, and the mixture reacted at room temperature for 12 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil led to the determination that the desired 2-oxo-3-propargyl-3-phenylhexynoic acid formed in a yield of 75 %.

$^1$H-NMR spectrum (CDCl$_3$, ppm): δ00(2H, t, J=2.5Hz), 3.06(2H, dd, J=2.5 and 16.0Hz), 3.48(2H, dd, J=2.5 and 1.60Hz), 7.25(5H, m), 10.22(1H, s).

A 1N aqueous solution of sodium hydroxide (5 ml; 5 mmoles) was added to this product, and the mixture was concentrated under reduced pressure. Ether was added, and the precipitated white solid was isolated by filtration to give 0.99 g (3.8 mmoles) of sodium 2-oxo-propargyl-3-phenylhexynoate in a yield of 5 %.

Melting point: 258°–266° C.

$^1$H-NMR spectrum (CDCl$_3$-DMSO-d$_6$, ppm): δ2.60(2H, t, J=2.5Hz), 2.94(2H, dd, J=2.5 and 16.0Hz), 3.45(2H, dd, J=2.5 and 16.0Hz), 7.26(5H, m).

IR spectrum (KBr, cm$^{-1}$) 3340, 2150, 1720, 1610.

Elemental analysis values (calculated, C$_{15}$H$_{11}$O$_3$Na, %): C, 68.65(68.70); H, 4.32(4.23).

EXAMPLE 90

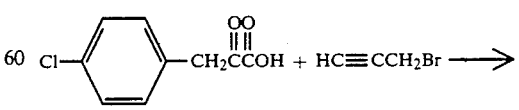

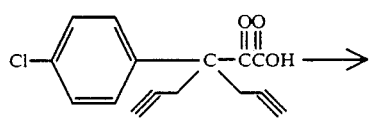

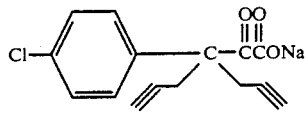

A 3N aqueous solution (5.0 ml) of sodium hydroxide and 10 ml of tetrahydrofuran were added to 0.99 g (5.0 mmoles) of p-chlorophenylpyruvic acid, and the mixture was stirred until a completely uniform solution formed. Then, 50 mg of triethyl ammonium chloride and 0.45 ml (6.0 mmoles) of propargyl bromide were added, and the mixture reacted at room temperature for 9 hours. The reaction mixture was acidified with 1N hydrochloric acid and extracted with ether. The ether layer was dried over magnesium sulfate. The drying reagent was separated by filtration, and the solvent was evaporated. The NMR spectrum of the resulting oil led to the determination that the desired 2-oxo-3-propargyl-3-(p-chlorophenyl)-hexynoic acid formed.

$^1$H-NMR spectrum (CDCl$_3$, ppm): δ2.87(2H, t, J=2.5Hz), 2.97(2H, dd, J=2.5 and 16.0Hz), 3.33(2H, dd, J=2.5 and 1.60Hz), 7.22(4H., s).

A 1N aqueous solution (1.5 ml) of sodium hydroxide was added to this product, and the mixture was concentrated under reduced pressure. Ether was added, and the precipitated white solid was isolated by filtration to give sodium 2-oxo-3-propargyl-3-(p-chlorophenyl)-5-hexynoate (0.66 g; 2.09 mmoles) in a yield of 42%.

Melting point: 252°–258° C.

$^1$H-NMR spectrum (CDCl$_3$-DMSO-d$_6$, ppm): δ2.45(2H, t, J=2.5Hz), 2.88(2H, dd, J=2.5 and 16.0Hz), 3.40(2H, dd, J=2.5 and 16.0Hz), 7.21(4H, s).

IR spectrum (KBr, cm$^{-1}$) 3350, 2160, 1720, 1650.

EXAMPLE 91

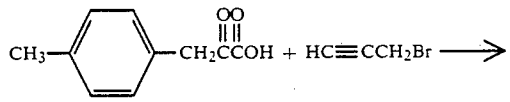

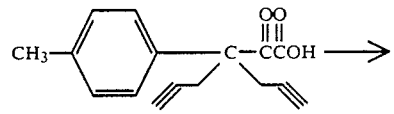

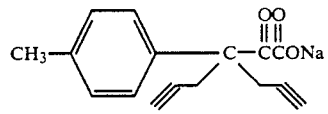

A 3N aqueous solution (5 ml) and 10 ml of tetrahydrofuran were added to 0.89 g (5.0 mmoles) of p-methylphenylpyruvic acid, and the mixture was stirred until a completely uniform solution formed. Then, 50 mg of triethyl ammonium chloride and 0.45 ml (6 mmoles) of propargyl bromide were added, and the mixture reacted at room temperature for 9 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oil led to the determination that the desired 2-oxo-3-propargyl-3-(p-methylphenyl)-hexynoic acid formed in a yield of 60 %.

$^1$H-NMR spectrum (CDCl$_3$, TMS, ppm): δ2.28(3H, s), 2.45(2H, m), 2.88(2H, dd, J=2.5 and 16.0Hz), 3.22(2H, dd, J=2.5 and 1.60Hz), 7.00(4H, s).

Then, 1.5 ml of a 1N aqueous solution of sodium hydroxide was added, and the mixture was concentrated under reduced pressure. Ether was added, and the precipitated white solid was isolated by filtration to give sodium 2-oxo-3-propargyl-3-(p-chlorophenyl)-5-hexynoate (0.74 g; 2.9 mmoles) was obtained in a yield of 59 %.

Melting point: 236°–242° C.

$^1$H-NMR spectrum (CDCl$_3$-DMSO-d$_6$, ppm): δ2.22(3H, s), 2.46(2H, t, J=2.5Hz), 2.86(2H, dd, J=2.5 and 16.0Hz), 3.40(2H, dd, J=2.5 and 16.0Hz), 7.03(4H, s).

IR spectrum (KBr, cm$^{-1}$) 3350, 2150, 1720, 1680.

Elemental analysis values (calculated, C$_{16}$H$_{13}$O$_3$·Na•2H$_2$O, %): C, 61.94(61.54); H, 5.47(5.49).

EXAMPLE 92

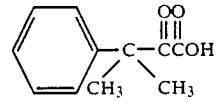

A 1N aqueous solution (20 ml) of sodium hydroxide was added to sodium phenylpyruvate (1.86 g, 10 mmoles), and the mixture was stirred until a completely uniform solution formed. Then, 1.5 ml (24 mmoles) of methyl iodide was added, and the mixture was stirred at room temperature for 12 hours. The reaction mixture was acidified with 1N hydrochloric acid, and extracted with 100 ml of ether. The ether layer was dried with magnesium sulfate. The drying reagent was separated by filtration, and the solvent was evaporated. The NMR spectral analysis of the resulting oil led to the determination that 2-oxo-3-methyl-3-phenylbutanoic acid formed in a yield of 42 %.

EXAMPLE 93

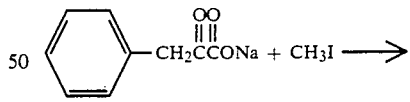

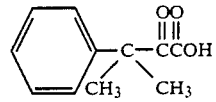

A 1N methanol solution (20 ml) of sodium hydroxide was added to 1.86 g (10 mmoles) of sodium phenylpyruvate and the mixture was stirred until a completely uniform solution formed. Then, 1.5 ml (24 mmoles) of methyl iodide was added, and the mixture was stirred at room temperature for 6 hours. The reaction mixture was acidified with 1N hydrochloric acid and extracted with 100 ml of ether. The ether layer was dried over magnesium sulfate. The drying reagent was separated by filtration, and the solvent was evaporated. The NMR spectral analysis of the resulting oily product led to the determination that 2-oxo-3-methyl-3-phenylbutanoic acid formed in a yield of 68 %.

EXAMPLE 94

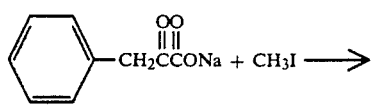

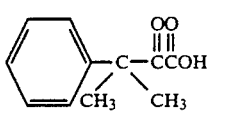

A 1N methanolic solution (20 ml) of sodium hydroxide and 10 ml of tetrahydrofuran were added to 1.86 g (10 mmoles) of sodium phenylpyruvate, and the mixture was stirred until a completely uniform solution formed. Then, 1.5 ml (24 mmoles) of methyl iodide was added, and the mixture was stirred at room temperature for 6 hours. The reaction mixture was acidified with 1N hydrochloric acid and extracted with 100 ml of ether. The ether layer was dried over magnesium sulfate. The drying reagent was separated by filtration, and the solvent was evaporated. The NMR spectral analysis of the resulting oily product led to the determination that 2-oxo-3-methyl-3-phenylbutanoic acid formed in a yield of 65 %.

EXAMPLE 95

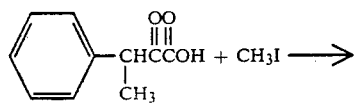

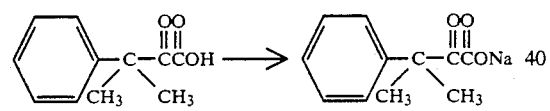

A 1N aqueous solution (30 ml) of sodium hydroxide was added to 1.78 g (10 mmoles) of 2-oxo-3phenylbutanoic acid, and the mixture was stirred until a completely uniform solution formed. Then, 1.0 ml (16 mmoles) of methyl iodide was added, and the mixture reacted at room temperature for 12 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that 2-oxo-3-methyl-3-phenyl-butanoic acid formed in a yield of 85 %.

$^1$H-NMR spectrum (CDCl$_3$, ppm): δ1.60(6H, s), 7.20(5H, s).

A 1N aqueous solution (8.5 ml) of sodium hydroxide was added to this product, and the mixture was concentrated under reduced pressure. Ether was added, and the precipitated white solid was isolated by filtration to give sodium 2-oxo-3-methyl-3-phenylbutanoate (1.22 g; 6.4 mmoles) in a yield of 64 %.

Melting point: 232°–238° C.

$^1$H-NMR spectrum (CDCl$_3$-DMSO-d$_6$, ppm): δ1.53(6H, s), 7.23(5H, m).

IR spectrum (KBr, cm$^{-1}$) 1720, 1680.

EXAMPLE 96

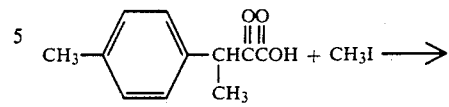

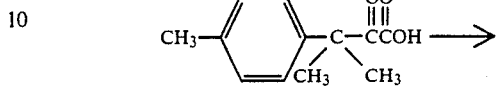

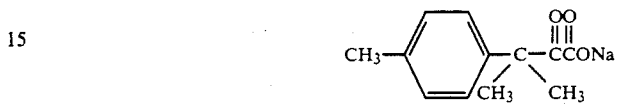

A 1N aqueous solution (15 ml) of sodium hydroxide and 30 ml of tetrahydrofuran were added to 0.96 g (5.0 mmoles) of 2-oxo-3-(p-methylphenyl)butanoic acid, and the mixture was stirred until a completely uniform solution formed. Then, 0.5 ml (8.0 mmoles) of methyl iodide was added, and the mixture reacted at room temperature for 15 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oily product led to the determination that 2-oxo-3-methyl-3-phenylbutanoic acid formed in a yield of 62%.

$^1$H-NMR spectrum (CDCl$_3$, ppm): δ1.60(6H, s), 2.25(3H, s), 7.23(5H, m).

Then, 3.5 ml of a 1N aqueous solution of sodium hydroxide was added to this product, and the mixture was concentrated under reduced pressure. Ether was added, and the precipitated white solid was isolated by filtration to give sodium 2-oxo-3-methyl-3-phenylbutanoate (0.48 g; 2.1 mmoles) in a yield of 42 %.

Melting point: 235°–242° C.

$^1$H-NMR spectrum (CDCl$_3$-DMSO-d$_6$, ppm): δ1.56(6H, s), 2.67(3H, s), 6.98(2H, d, J=8.0Hz), 7.28(2H, d, J=8.0Hz).

IR spectrum (KBr, cm$^{-1}$) 1700, 1660.

EXAMPLE 97

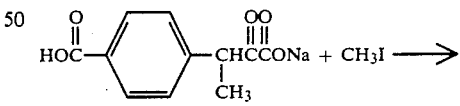

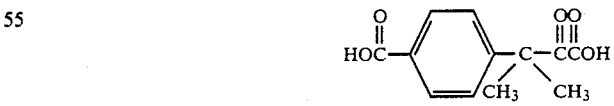

A 2N aqueous solution (30 ml) of sodium hydroxide and 50 ml of tetrahydrofuran were added to 2.22 g (10 mmoles) of 2-oxo-3-(p-carboxyphenyl)butanoic acid, and the mixture was stirred until a completely uniform solution formed. Then, 1.5 ml (24 mmoles) of methyl iodide was added, and the mixture reacted at room temperature for 24 hours. The reaction mixture was acidified with 1N hydrochloric acid, and extracted with ether. The ether layer was dried. The drying reagent was separated by filtration, and the solvent was evaporated. The NMR spectral analysis of the resulting oily product led to the determination that the desired 2-oxo-3-methyl-3-phenylbutanoic acid formed in a yield of 80 %. This product was converted to a methyl ester by using diazomethane, and isolated and purified by silica gel column chromatography (ethyl acetate:hexane=1:10). Then a 1N aqueous solution of sodium hydroxide was added and the ester was hydrolyzed. The hydrolyzate was acidified with 1N hydrochloric acid and extracted with ether. After drying, the solvent was evaporated to give 0.80 g (3.4 mmoles) of 2-oxo-3-methyl-3-(p-carboxyphenyl)butanoic acid as a white solid in a yield of 34 %.

Melting point: 144°–163° C.

$^1$H-NMR spectrum (CDCl$_3$-DMSO-d$_6$, ppm): δ1.62(6H, s), 7.30(2H, d, J=8.0Hz), 8.00(2H, d, J=8.0Hz), 9.10(2H, br s).

IR spectrum (KBr, cm$^{-1}$) 3540, 1703, 1680.

EXAMPLE 98

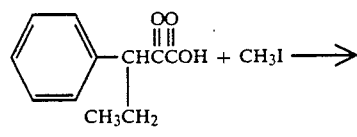

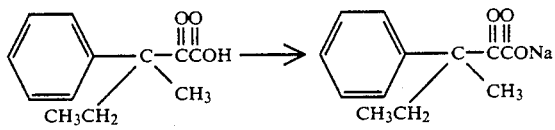

A 3N aqueous solution (0.84 ml) of sodium hydroxide and 3.0 ml of tetrahydrofuran were added to 0.30 g (1.39 mmoles) of sodium 2-oxo-3-phenylpentanoate, and the mixture was stirred until a completely uniform solution formed. Then, 0.23 mg (2.8 mmoles) of methyl iodide and 36 mg (0.16 mmole) of triethylbenzylammonium chloride were added, and the mixture reacted at room temperature for 7 hours. The reaction mixture was acidified with 1N hydrochloric acid and extracted with ether. The ether layer was dried over magnesium sulfate. The drying reagent was separated by filtration, and the solvent was evaporated. The NMR spectral analysis of the resulting oily product led to the determination that the desired 2-oxo-3-methyl-3-phenylpentanoic acid formed in a yield of 62 %. Then, 1.2 ml of a 1N aqueous solution of sodium hydroxide was added to this product, and the mixture was concentrated under reduced pressure. Ether was added, and the precipitated white solid was isolated by filtration to give 0.15 g (0.63 mmole) of sodium 2-oxo-3-methyl-3-phenylpentanoate in a yield of 46 %.

Melting point: 231°–236° C.

$^1$H-NMR spectrum (CDCl$_3$-DMSO-d$_6$, ppm): δ0.51(3H, t, J=7.5Hz), 1.78(3H, s), 2.62(2H, q, J=7.5Hz), 6.88(5H, br s).

IR spectrum (KBr, cm$^{-1}$) 1708, 1640, 1390.

EXAMPLE 99

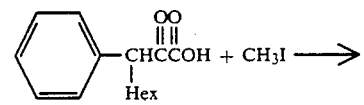

-continued

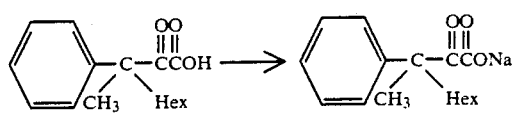

A 3N aqueous solution (0.50 ml) of sodium hydroxide and 2.0 ml of tetrahydrofuran were added to 0.205 g (0.76 mmoles) of sodium 2-oxo-3-phenylnonanoate, and the mixture was stirred until a completely uniform solution formed. Then, 0.09 ml (1.8 mmoles) of methyl iodide and 20 mg of triethylbenzylammonium chloride were added, and the mixture reacted at room temperature for 23 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that the desired 2-oxo-3-methyl-3-phenylnonanoic acid formed in a yield of 52%. Then, 1.0 ml of a 1N aqueous solution of sodium hydroxide was added to this product, and the mixture was concentrated under reduced pressure. Ether was added, and the precipitated white solid was isolated by filtration to give sodium 2-oxo-3-methyl-3-phenylnonanoate (0.065 g; 0.229 mmole) in a yield of 58 %.

Melting point: 238°–242° C.

$^1$H-NMR spectrum (CDCl$_3$-DMSO-d$_6$, ppm): δ1.81(3H, br t), 0.95-1.45(10H, br s), 1.56(3H, s), 7.20-7.34(5H, s).

IR spectrum (KBr, cm$^{-1}$) 1690, 1640, 1385.

EXAMPLE 100

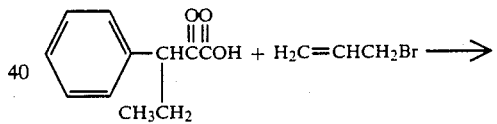

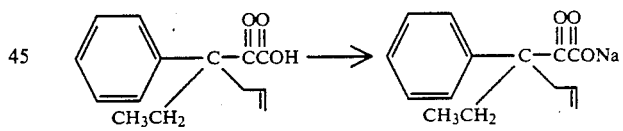

A 3N aqueous solution (0.76 ml) of sodium hydroxide and 3.0 ml of tetrahydrofuran were added to 0.30 g (1.39 mmoles) of sodium 2-oxo-3-phenylpentanoate, and the mixture was stirred until a completely uniform solution formed. Then, 0.24 ml (2.8 mmoles) of allyl bromide and 36 mg (0.16 mmole) of triethylbenzylammonium chloride were added, and the mixture reacted at room temperature for 25 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that 2-oxo-3-ethyl-3-phenyl-5-hexynoic acid formed in a yield of 80 %. Then, 1.3 ml of a 1N aqueous solution of sodium hydroxide was added to this product, and the mixture was concentrated under reduced pressure. Ether was added, and the precipitated white solid was isolated by filtration to give 0.086 g (0.34 mmole) of sodium 2-oxo-3-ethyl-3-phenyl-5-hexynoate formed in a yield of 24 %.

Melting point: 218°-221° C.

$^1$H-NMR spectrum (CDCl$_3$-DMSO-d$_6$, ppm): 0.80(3H, t, J=7.5Hz), 1.81-2.41(2H, m), 2.90(2H, q, J=7.5Hz), 4.95(1H, dd, J=1.5 and 9.2Hz), 5.05(1H, dd, J=1.5 and 5.5Hz), 5.28-5.80(1H, m), 7.20-7.40(5H, m).

IR spectrum (KBr, cm$^{-1}$) 1685, 1640, 1400.

EXAMPLE 101

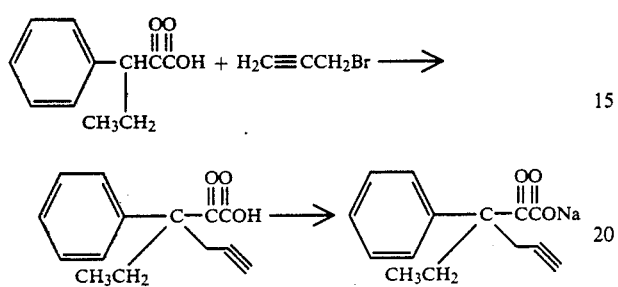

A 3N aqueous solution (0.84 ml) of sodium hydroxide and 3.0 ml of tetrahydrofuran were added to 0.30 g (1.39 mmoles) of 2-oxo-3-phenylpentanoic acid, and the mixture was stirred until a completely uniform solution formed. Then, 0.21 ml (2.3 mmoles) of propargyl bromide and 30 mg (0.13 mmole) of triethylbenzylammonium chloride were added, and the mixture was reacted at room temperature for 24 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that the desired 2-oxo-3-ethyl-3-phenyl-5-hexynoic acid formed in a yield of 50 %. This product was isolated as a pure sodium salt by using an aqueous solution of sodium hydroxide.

Melting point: 210°-214° C.

$^1$H-NMR spectrum (CDCl$_3$-DMSO-d$_6$, ppm): δ0 83(3H, t, J=7.5Hz), 3.04(2H, q, J=7.5Hz), 3.25(2H, d, J=2.2Hz), 3.45(1H, t, J=2.5Hz), 7.30(5H, m), 9.50(1H, br s).

IR spectrum (KBr, cm$^{-1}$) 3100, 1690, 1630.

EXAMPLE 102

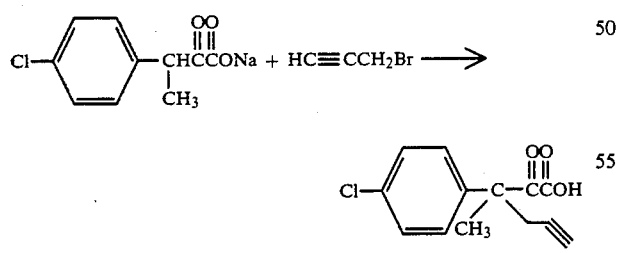

A 3N aqueous solution (1.0 ml) of sodium hydroxide and 5.0 ml of tetrahydrofuran were added to 0.57 g (2.4 mmoles) of sodium 2-oxo-3-(p-chlorophenyl)butanoate, and the mixture was stirred until a completely uniform solution formed. Then, 0.20 ml (2.7 mmoles) of propargyl bromide and 24 ml of triethylbenzylammonium chloride were added, and the mixture reacted at room temperature for 12 hours. The reaction mixture was acidified with 1N hydrochloric acid and extracted with ether. The ether layer was dried over magnesium sulfate. The drying reagent was separated by filtration, and the solvent was evaporated. The resulting oily product was purified to give the desired 2-oxo-3-(p-chlorophenyl)-hexynoic acid in a yield of 66 %.

$^1$H-NMR spectrum (CDCl$_3$-DMSO-d$_6$, ppm): δ1.78(3H, s), 1.97(1H, t, J=2.5Hz), 2.77(1H, dd, J=2.5 and 16.0Hz), 3.20(1H, dd, J=2.5 and 16.0Hz), 7.27(4H, s), 9.97(1H, br s).

IR spectrum (KBr, cm$^{-1}$) 2100, 1705, 1640, 1380.

EXAMPLE 103

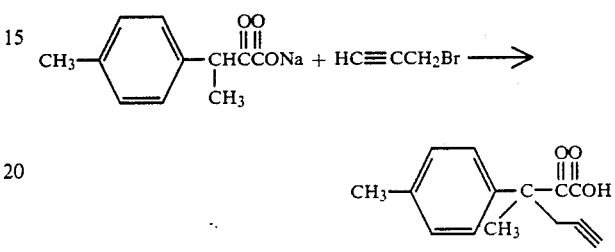

A 3N aqueous solution (0.9 ml) of sodium hydroxide and 5.0 ml of tetrahydrofuran were added to 0.50 g (2.6 mmoles) of sodium 2-oxo-3-(p-methylphenyl)butanoate, and the mixture was stirred until a completely uniform solution formed. Then, 0.20 ml (2.7 mmoles) of propargyl bromide and 26 mg of triethylbenzylammonium chloride were added, and the mixture was reacted at room temperature for 12 hours. The reaction mixture was acidified with 1N hydrochloric acid and extracted with ether. The ether layer was dried over magnesium sulfate. The drying reagent was separated by filtration, and the solvent was evaporated. The resulting solid was purified to obtain 2-oxo-3-(p-methylphenyl)-5-hexynoic acid in a yield of 52 %.

$^1$H-NMR spectrum (CDCl$_3$-DMSO-d$_6$, ppm) δ1.78(3H, s), 1.93(1H, t, J=2.5Hz), 2.34(3H, s), 2.71(1H, dd, J=2.5 and 16.0Hz), 3.12(1H, dd, J=2.5 and 16.0Hz), 7.24(4H, s).

IR spectrum (KBr, cm$^{-1}$) 1700, 1640, 1380.

EXAMPLE 104

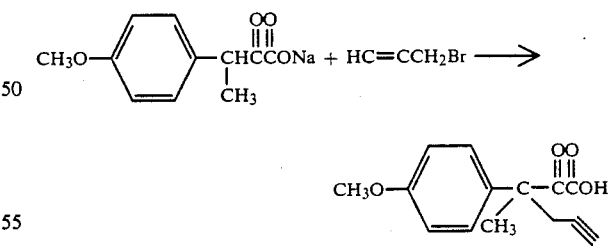

A 1N aqueous solution (5.0 ml) of sodium hydroxide and 10 ml of tetrahydrofuran were added to 0.15 g (0.69 mmole) of sodium 2-oxo-3-(p-methoxyphenyl)butanoate, and the mixture was stirred until a completely uniform solution formed. Then, 0.31 ml of propargyl bromide and 10 ml of cetyltrimethylammonium chloride were added, and the mixture was reacted at room temperature for 12 hours. The reaction mixture was acidified with 1N hydrochloric acid and extracted with ether. The ether layer was dried over magnesium sulfate. The drying reagent was separated by filtration, and the solvent was evaporated. The NMR spectral analysis led to the determination that 2-oxo-3-(p-methoxyphenyl)-5-hexynoic acid formed in a yield of 47 %.

$^1$H-NMR spectrum (CDCl$_3$-DMSO-d$_6$, ppm): δ1.43(3H, s), 1.97(1H, t, J=2.5Hz), 2.72(1H, dd, J=2.5 and 16.0Hz), 3.15(1H, dd, J=2.5 and 16.0Hz), 3.75(3H, s), 6.77(2H, d, J=8.0Hz), 7.08(2H, d, J=8.0Hz).

EXAMPLE 105

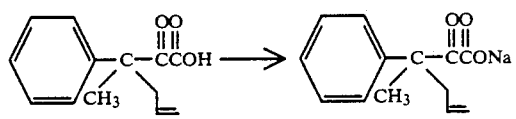

A 3N aqueous solution (0.61 ml) of sodium hydroxide and 2.0 ml of tetrahydrofuran were added to 0.15 g (0.71 mmole) of 2-oxo-3-phenyl-5-hexynoic acid, and the mixture was stirred until a completely uniform solution formed. Then, 0.091 ml (1.47 mmoles) of methyl iodide and 19 mg (0.083 mmole) of triethylbenzylammonium chloride were added, and the mixture was reacted at 40° C. for 16 hours. The reaction mixture was acidified with 1N hydrochloric acid, and extracted with ether. The ether layer was dried over magnesium sulfate. The drying reagent was separated by filtration, and the solvent was evaporated. The NMR spectral analysis of the resulting oily product led to the determination that 2-oxo-3-ethyl-3-phenyl-5-hexynoic acid formed in a yield of 62 %. Then, 0.35 ml of a 1N aqueous solution of sodium hydroxide was added, and the mixture was concentrated under reduced pressure. Ether was added, and the precipitated white solid was isolated by filtration to give 0.066 g (0.302 mmole) of sodium 2-oxo-3-ethyl-3-phenyl-5-hexynoate in a yield of 41 %.

Melting point: 224°–228° C.

$^1$H-NMR spectrum (CDCl$_3$-DMSO-d$_6$, ppm): δ1.60(3H, s), 2.50–3.05(2H, m), 4.95(1H, dd, J=1.5 and 9.5Hz), 5.05(1H, dd, J=1.5 and 4.9Hz), 5.28–5.80(1H, m), 7.15–7.50(5H, m).

IR spectrum (KBr, cm$^{-1}$) 1680, 1610, 890.

EXAMPLE 106

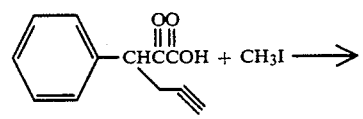

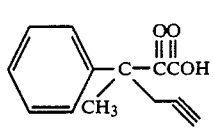

A 3N methanolic solution (4.0 ml) of sodium hydroxide and 10 ml of methanol were added to 1.01 g (5.0 mmoles) 2-oxo-3-phenyl-5-hexynoic acid, and the mixture was stirred until a completely uniform solution formed. Then, with ice cooling, 0.4 ml (6 mmoles) of methyl iodide and 50 mg of triethylbenzylammonium chloride were added, and the mixture reacted for 9 hours while its temperature was gradually elevated to room temperature. The reaction mixture was acidified with 1N hydrochloric acid, and extracted with ether. The ether layer was dried over magnesium sulfate. The drying agent was separated by filtration, and the solvent was evaporated. The NMR spectral analysis of the resulting oily product led to the determination that the desired 2-oxo-3-methyl-3-phenyl-5-hexynoic acid formed in a yield of 42%.

$^1$H-NMR spectrum (CDCl$_3$-DMSO-d$_6$, ppm): δ1.80(3H, s), 1.92(1H, t, J=2.5Hz), 2.77(1H, dd, J=2.5 and 16.0Hz), 3.17(1H, dd, J=2.5 and 16.0Hz), 7.23(5H, s).

EXAMPLE 107

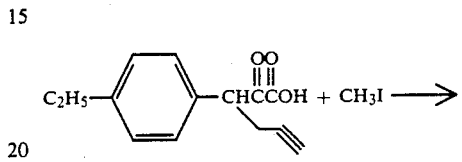

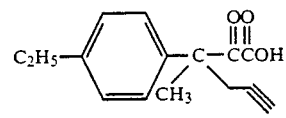

A 3N aqueous solution (4.0 ml) of sodium hydroxide and 5.0 ml of tetrahydrofuran were added to 0.53 g (2.3 mmoles) of 2-oxo-3-(p-ethylphenyl)-5-hexynoic acid, and the mixture was stirred until a completely uniform solution formed. Then, with ice cooling, 0.2 ml (3.0 mmoles) of methyl iodide and 23 mg of triethylbenzylammonium chloride were added, and the mixture reacted for 9 hours while gradually elevating its temperature to room temperature. The reaction mixture was acidified with 1N hydrochloric acid, and extracted with ether. The ether layer was dried over magnesium sulfate. The drying agent was separated by filtration, and the solvent was evaporated. The NMR spectral analysis of the resulting oily product led to the determination that the desired 2-oxo-3-methyl-3-(p-ethylphenyl)-5-hexynoic acid formed in a yield of 46 %.

$^1$H-NMR spectrum (CDCl$_3$-DMSO-d$_6$, ppm): δ1.17(3H, t, J=7.2Hz), 1.78(3H, s), 2.14(1H, t, J=2.5Hz), 2.58(2H, q, J=7.4Hz), 2.71(1H, dd, J=2.5 and 16.0Hz), 3.12(1H, dd, J=2.5 and 16.0Hz), 7.24(4H, s).

EXAMPLE 108

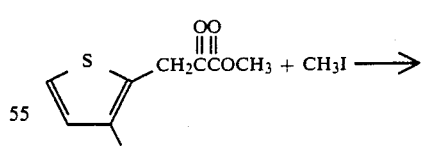

A 1N aqueous solution of sodium hydroxide (16.8 ml; 50.4 mmoles) was added to 0.5 g (2.5 mmoles) of methyl 3-methyl-2-thienylpyruvate, and the mixture was stirred at room temperature until the mixture became uniform. Then, 3.67 g (50.4 mmoles) of methyl iodide was added, and the mixture was stirred at room temperature for 10 hours. The reaction mixture was acidified with 1N hydrochloric acid. The ether layer was dried over magnesium sulfate, and the solvent was evaporated to give a yellowish brown oily product. This product was purified by silica gel column chromatography (hexane:ethyl acetate=5:1) to give 2-oxo-3-methyl-3-(3-methyl-2-thienyl)butanoic acid (1.026 g; 4.8 mmoles) in a yield of 48 %.

$^1$H-NMR spectrum (CDCl$_3$, TMS, ppm): δ1.67(6H, s), 2.02(3H, s), 6.73(1H, d, J=4.8Hz), 9.25-9.50(1H, br s).

Industrial Utilizability

According to the method of this invention, 2-oxo-3-aromatic carboxylic acids can be synthesized in good yields with good selectivity. The 2-oxo-3-aromatic carboxylic acid derivatives obtained by this invention can be easily converted to aromatic amino acids by reductive animation of the carbonyl group at the 2-position by known methods. Accordingly, this invention can also provide a simple process for producing such aromatic amino acid derivatives. Furthermore, by oxidatively decarboxylating in a conventional manner 2-oxo-3-aromatic carboxylic acid derivatives obtained by this invention, 2-aromatic alkanoic acid derivatives, which are important as synthetic intermediates of medicines and agricultural chemicals, such as inflammatory analgesic agents or insecticides, can be produced.

We claim:

1. A process for producing 2-oxo-3-aromatic carboxylic acid derivatives represented by the following general formula

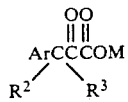 (IV)

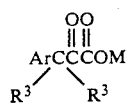 (V)

or

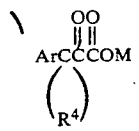 (VI)

wherein Ar represents an aromatic group, R$^2$ represents a hydrogen atom or a substituted or unsubstituted alkyl, cycloalkyl, alkenyl, alkynyl or aralkyl group, R$^3$ represents a substituted or unsubstituted alkyl, cycloalkyl, alkenyl, alkynyl or aralkyl group, R$^4$ represents a substituted or unsubstituted alkylene group having 2 or more carbon atoms, and M represents a hydrogen atom, an alkali metal or alkaline earth metal atom, which comprises reacting an aromatic pyruvic acid derivative represented by the following formula

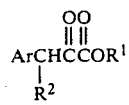 (I)

wherein Ar and R$^2$ are as defined above, and R$^1$ represents a hydrogen atom, a lower alkyl group, an alkali metal or alkaline earth metal atom, with an electrophilic compound represented by the general formula

 (II)

or

 (III)

wherein R$^3$ and R$^4$ are as defined above, and X$^1$ and X$^2$ each represent a leaving group,
in the presence of a base in a protic solvent.

2. The process of claim 1 in which the protic solvent is water, an alcoholic solvent or a mixture of water and an alcoholic solvent.

3. The process of claim 1 in which the protic solvent includes an aprotic solvent.

4. The process of claim 1 in which the base is selected from sodium hydroxide, potassium hydroxide, lithium hydroxide, calcium hydroxide and sodium methoxide.

5. The process of claim 1 in which the reaction is carried out at a temperature of not more than 100° C.

6. The process of claim 1 in which the reaction is carried out in the presence of a quaternary ammonium salt.

7. The process of claim 1 in which the aromatic pyruvic acid derivative of general formula (I) in which R$^2$ is a hydrogen atom is reacted with the electrophilic compound of general formula (II) to form the corresponding 2-oxo-3-aromatic carboxylic acid derivative of general formula (IV) in which R$^2$ represents a hydrogen atom.

8. The process of claim 7 in which the electrophilic compound is used in an amount of not more than 1 equivalent per equivalent of the aromatic pyruvic acid derivative.

9. The process of claim 7 in which the base is used in an amount of not more than 2 equivalents per equivalent of the aromatic pyruvic acid derivative.

10. The process of claim 1 in which the aromatic pyruvic acid derivative of general formula (I) in which R$^2$ is as defined above other than a hydrogen atom is reacted with the electrophilic compound of general formula (II) to produce the corresponding 2-oxo-3-aromatic carboxylic acid derivative represented by general formula (IV).

11. The process of claim 1 in which the aromatic pyruvic acid derivative of general formula (I) in which R$^2$ represents a hydrogen atom is reacted with the electrophilic compound of general formula (II) to form the corresponding 2-oxo-3-aromatic carboxylic acid derivative of general formula (V).

12. The process of claim 1 in which the aromatic pyruvic acid derivative of formula (I) in which R$^2$ represents a hydrogen atom is reacted with the electrophilic compound of general formula (III) to form the corresponding 2-oxo-3-aromatic carboxylic acid derivative of general formula (VI).

13. The process of claim 10, 11 or 12 in which the electrophilic compound and the base are used at least in stoichiometrical amounts.

* * * * *